(12) United States Patent
Fauth et al.

(10) Patent No.: US 12,408,952 B2
(45) Date of Patent: Sep. 9, 2025

(54) ARTHROPLASTY IMPLANTS, SYSTEMS, AND METHODS

(71) Applicant: RTG Scientific, LLC, Austin, TX (US)

(72) Inventors: Andrew Fauth, North Logan, UT (US);
Andrew Dickson, Knoxville, TN (US);
Richard Justin Hyer, Hyrum, UT (US)

(73) Assignee: RTG Scientific, LLC, Austin, TX (US)

( * ) Notice: Subject to any disclaimer, the term of this patent is extended or adjusted under 35 U.S.C. 154(b) by 625 days.

(21) Appl. No.: 17/668,315

(22) Filed: Feb. 9, 2022

(65) Prior Publication Data
US 2022/0265333 A1 Aug. 25, 2022

Related U.S. Application Data

(60) Provisional application No. 63/147,640, filed on Feb. 9, 2021.

(51) Int. Cl.
*A61B 17/86* (2006.01)
*A61B 17/70* (2006.01)
(Continued)

(52) U.S. Cl.
CPC ........ *A61B 17/704* (2013.01); *A61B 17/7032* (2013.01); *A61B 17/7034* (2013.01);
(Continued)

(58) Field of Classification Search
CPC . A61B 17/704; A61B 17/725; A61B 17/8605; A61B 17/8625; A61B 17/863;
(Continued)

(56) References Cited

U.S. PATENT DOCUMENTS

| 3,848,276 A | * | 11/1974 | Martinez | ................. A61F 2/384 |
| | | | | 623/20.26 |
| 4,810,149 A | | 3/1989 | Lee et al. | |

(Continued)

FOREIGN PATENT DOCUMENTS

GB 2033755 A 5/1980
WO 2004098442 A1 11/2004
(Continued)

OTHER PUBLICATIONS

U.S. Appl. No. 10/085,782, filed Oct. 2, 2018, Reed.
(Continued)

*Primary Examiner* — Jessica Weiss
(74) *Attorney, Agent, or Firm* — David Meibos; Maywood IP Law

(57) ABSTRACT

A bone implant may include a shaft having a proximal end, a distal end, a longitudinal axis, a proximal shaft portion, and a distal shaft portion. The proximal shaft portion may include a first minor diameter, and a first helical thread disposed about the proximal shaft portion defining a first major diameter. The first helical thread may include a first concave undercut surface. The distal shaft portion may include a second minor diameter, and a second helical thread disposed about the distal shaft portion defining a second major diameter. The second helical thread may include a second concave undercut surface. The first and second concave undercut surfaces may be angled towards the distal end of the shaft. The second minor diameter may be smaller than the first minor diameter and the second major diameter may be smaller than the first major diameter.

32 Claims, 23 Drawing Sheets

(51) Int. Cl.
*A61B 17/72* (2006.01)
*A61F 2/40* (2006.01)
*A61F 2/44* (2006.01)
*A61B 17/00* (2006.01)
*A61B 17/56* (2006.01)
*A61B 17/68* (2006.01)
*A61F 2/30* (2006.01)

(52) U.S. Cl.
CPC ........ *A61B 17/7037* (2013.01); *A61B 17/725* (2013.01); *A61B 17/8605* (2013.01); *A61B 17/8625* (2013.01); *A61B 17/863* (2013.01); *A61F 2/4014* (2013.01); *A61F 2/4081* (2013.01); *A61B 2017/00477* (2013.01); *A61B 2017/00526* (2013.01); *A61B 2017/564* (2013.01); *A61B 2017/681* (2013.01); *A61F 2002/30332* (2013.01); *A61F 2220/0033* (2013.01)

(58) Field of Classification Search
CPC ............ A61B 17/7037; A61B 17/7034; A61B 17/7032; A61B 2002/30332; A61B 2017/00477; A61B 2017/00526; A61B 2017/564; A61B 2017/681; A61F 2220/0033; A61F 2/4014; A61F 2/4081
USPC ...................... 623/19.11–19.14; 606/300–321
See application file for complete search history.

(56) References Cited

U.S. PATENT DOCUMENTS

| | | | |
|---|---|---|---|
| 5,964,768 A | 10/1999 | Huebner | |
| 6,743,233 B1* | 6/2004 | Baldwin | A61B 17/0401 606/232 |
| 6,800,078 B2 | 10/2004 | Reed | |
| 7,281,925 B2* | 10/2007 | Hall | A61C 8/0022 606/314 |
| 7,537,603 B2 | 5/2009 | Huebner et al. | |
| 8,337,205 B2* | 12/2012 | Reed | A61C 8/0086 433/174 |
| 8,602,781 B2 | 12/2013 | Reed | |
| 8,875,399 B2 | 11/2014 | Reed | |
| 9,079,263 B2 | 7/2015 | Reed | |
| 9,421,106 B2* | 8/2016 | Splieth | A61F 2/4081 |
| 9,526,547 B2 | 12/2016 | Reed | |
| 9,629,725 B2* | 4/2017 | Gargac | A61F 2/4081 |
| 9,687,319 B2 | 6/2017 | Reed | |
| 9,782,209 B2* | 10/2017 | Reed | A61B 17/863 |
| 9,901,379 B2 | 2/2018 | Reed | |
| 9,931,219 B2* | 4/2018 | Sikora | A61F 2/4618 |
| 10,085,782 B2 | 10/2018 | Reed | |
| 10,265,177 B2 | 4/2019 | Quinn et al. | |
| 10,441,385 B2 | 10/2019 | Reed | |
| 10,639,086 B2 | 5/2020 | Reed | |
| 10,687,877 B2 | 6/2020 | Lavigne et al. | |
| 2003/0088248 A1 | 5/2003 | Reed | |
| 2006/0003291 A1* | 1/2006 | Hall | A61C 8/0022 433/174 |
| 2006/0149265 A1 | 7/2006 | James et al. | |
| 2006/0204930 A1* | 9/2006 | Sul | A61C 8/0022 433/174 |
| 2007/0233123 A1 | 10/2007 | Ahmad et al. | |
| 2009/0069852 A1 | 3/2009 | Farris et al. | |
| 2009/0305189 A1 | 12/2009 | Scortecci et al. | |
| 2010/0094349 A1* | 4/2010 | Hammer | A61B 17/7035 606/279 |
| 2010/0094358 A1 | 4/2010 | Moore et al. | |
| 2010/0121327 A1 | 5/2010 | Velikov | |
| 2011/0276095 A1* | 11/2011 | Bar | A61B 17/863 606/279 |
| 2011/0288650 A1 | 11/2011 | Ries et al. | |
| 2012/0253467 A1* | 10/2012 | Frankle | A61F 2/40 623/19.11 |
| 2013/0253517 A1* | 9/2013 | Mitchell | A61B 17/1671 606/79 |
| 2014/0023990 A1* | 1/2014 | Zadeh | A61B 17/863 433/174 |
| 2014/0056460 A1 | 2/2014 | Barnes | |
| 2014/0058460 A1* | 2/2014 | Reed | A61B 17/863 606/301 |
| 2014/0329202 A1 | 11/2014 | Zadeh | |
| 2015/0230843 A1 | 8/2015 | Palmer et al. | |
| 2018/0303529 A1 | 10/2018 | Zastrozna | |
| 2018/0335070 A1 | 11/2018 | May | |
| 2019/0038426 A1 | 2/2019 | Ek | |
| 2019/0105131 A1 | 4/2019 | Barton et al. | |
| 2019/0223917 A1 | 7/2019 | Gray et al. | |
| 2019/0262047 A1 | 8/2019 | Sommers et al. | |
| 2019/0358039 A1 | 11/2019 | Ducharme et al. | |
| 2020/0030108 A1* | 1/2020 | Orphanos | A61F 2/4014 |
| 2021/0259842 A1 | 8/2021 | Feng et al. | |
| 2022/0249148 A1 | 8/2022 | Hyer et al. | |

FOREIGN PATENT DOCUMENTS

| | | |
|---|---|---|
| WO | 2007074498 A2 | 7/2007 |
| WO | 2019238085 A2 | 12/2019 |
| WO | 2020224657 A2 | 11/2020 |

OTHER PUBLICATIONS

International Search Report and Written Opinion dated Jul. 6, 2022 for corresponding PCT Application No. PCT/US2022/015866.
International Search Report dated Aug. 10, 2023 for corresponding PCT/US2023/020900.
International Search Report dated Jul. 5, 2023 for corresponding PCT/US2023/018561.
Supplementary European Search Report mailed Dec. 23, 2024 for corresponding European Patent Application No. 22753293.4.

* cited by examiner

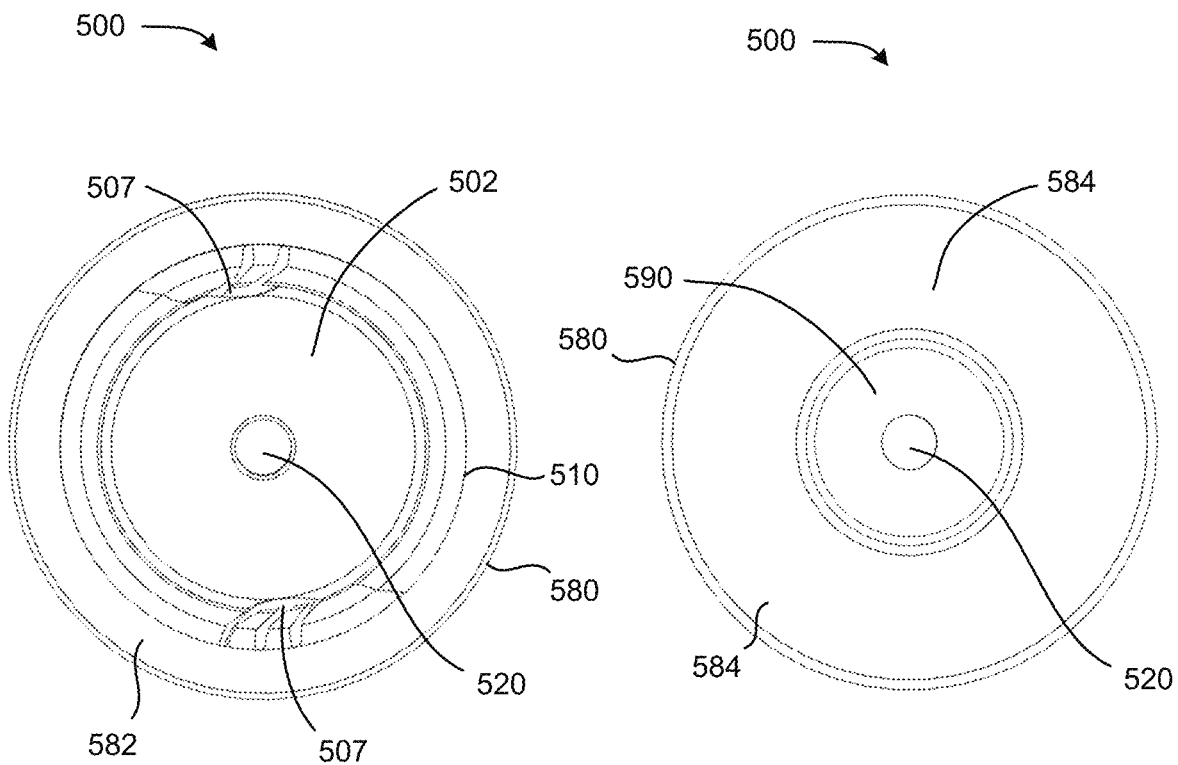
FIG. 5C
FIG. 5D
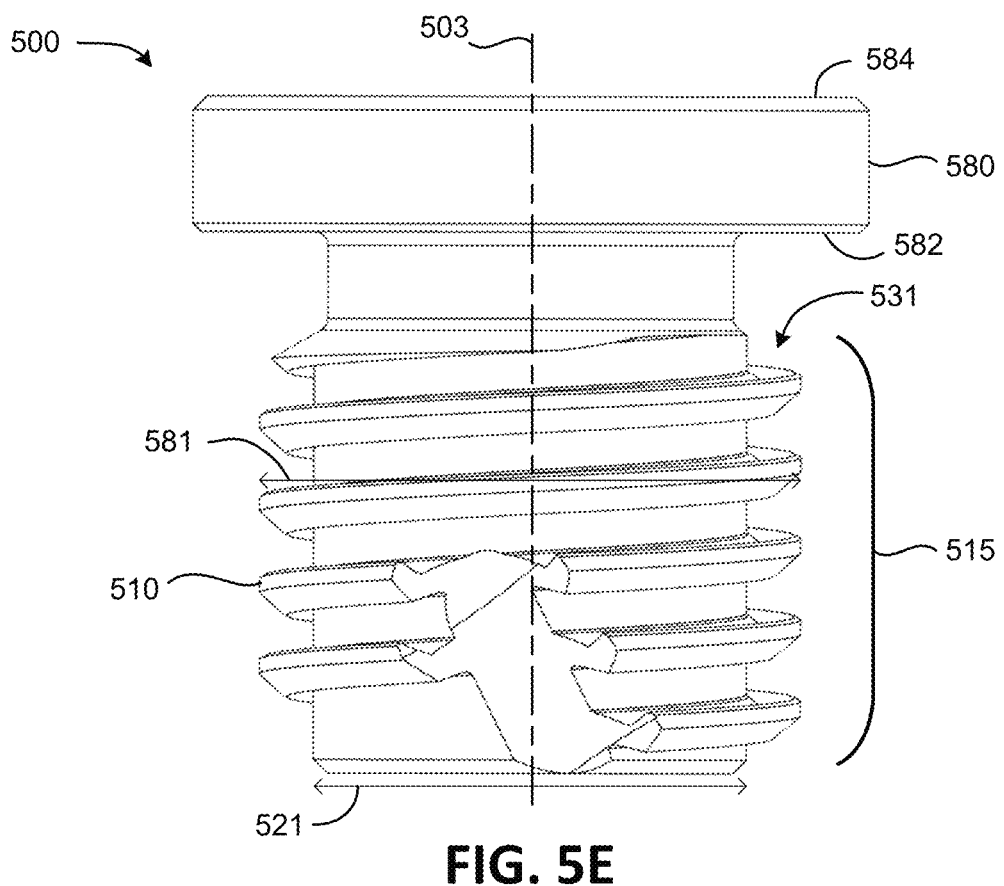
FIG. 5E

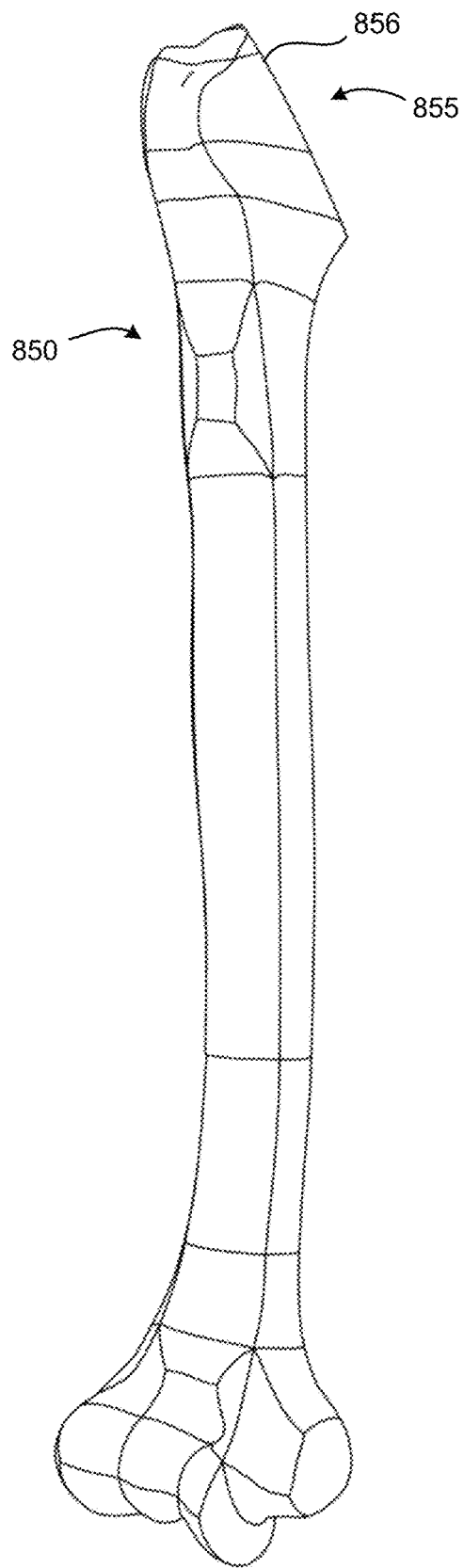 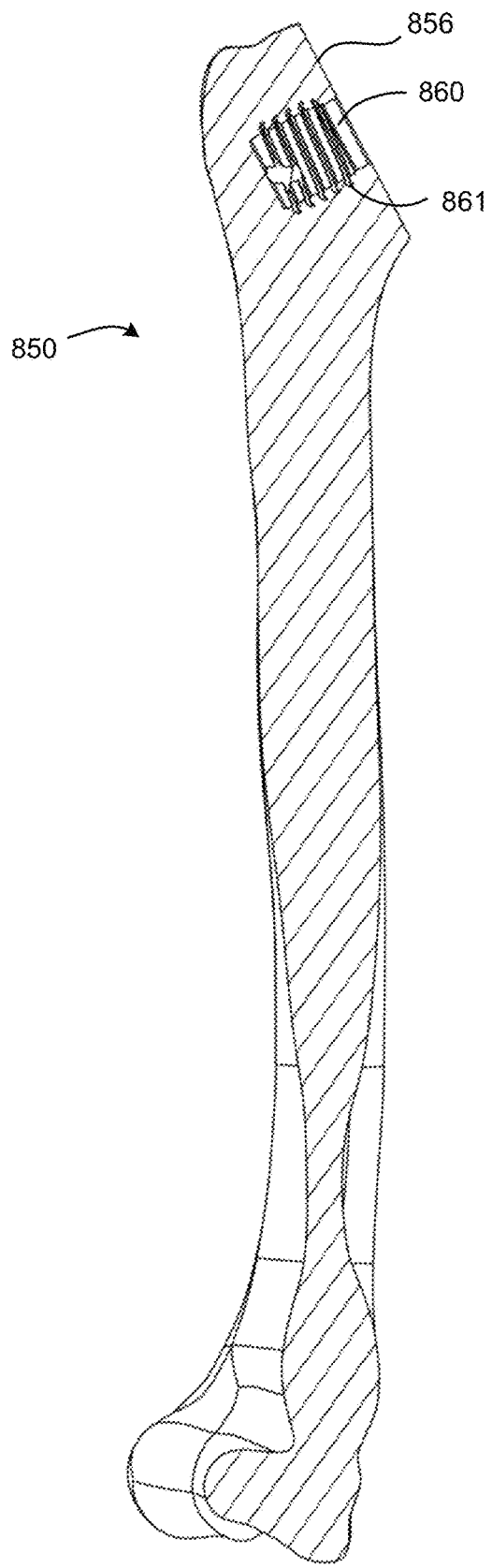
FIG. 15  FIG. 16

ARTHROPLASTY IMPLANTS, SYSTEMS, AND METHODS

CROSS-REFERENCE TO RELATED APPLICATIONS

This application claims the benefit of U.S. Provisional Patent Application Ser. No. 63/147,640 filed on Feb. 9, 2021, entitled "FASTENING DEVICES, SYSTEMS, AND METHODS". The foregoing document is hereby incorporated by reference in its entirety.

TECHNICAL FIELD

The present disclosure relates to joint arthroplasty implants. More specifically, the present disclosure relates to shoulder arthroplasty implants with improved thread designs and morphology. While the present disclosure is made in the context of humeral and glenoid implants for shoulder arthroplasty, the disclosed principles are applicable to arthroplasty implants for other locations.

BACKGROUND

Joint arthroplasty procedures are conducted to restore the function of an unhealthy joint. Typically, these procedures involve replacing the unhealthy natural articulating surfaces of the joint with artificial articulating surfaces. The new artificial articulating surfaces are typically anchored into the adjacent bones to maintain long term stability. However, joint arthroplasty devices implanted within bone can become lose over time due to multi-axial forces and off-axis loading scenarios that may be applied to the joint arthroplasty device during the healing process. Joint arthroplasty devices utilizing traditional thread designs, tapered stems, keels, or other methods may not provide sufficient fixation to overcome these multi-axial forces and off-axis loading scenarios. Accordingly, joint arthroplasty devices with improved thread designs for increasing bone fixation and load sharing between a bone/implant interface experiencing multi-axial and off-loading conditions would be desirable.

In shoulder arthroplasty, a humeral implant is attached to the humerus, and a glenoid implant is attached to the glenoid or scapula. There are two different main categories of shoulder arthroplasty: anatomic and reverse. In an anatomic procedure, the implant designs are intended to replicate the natural anatomy. The humeral head is replaced with a similarly shaped convex hemispherical surface, while the glenoid is replaced with a shallow concave socket. In a reverse procedure, the natural ball and socket is reversed. The humeral head is replaced with a socket fixed to the humerus and the glenoid is replaced with a ball (or glenosphere) fixed to the scapula.

Regardless of the type of procedure, fixation of the humeral component into the humerus typically involves an implant with a shaft portion that extends into the metaphysis and optionally into the diaphysis of the humerus. The goals of these implants are to preserve as much native bone as possible, maximize the mechanical stability of the implants, and allow for more physiological loading of the bone to preserve long-term fixation.

The present disclosure is made in the context of humeral and glenoid implants for shoulder arthroplasty. Other applications may include a femoral implant for hip or knee arthroplasty, a tibial implant for knee or ankle arthroplasty, implants for the elbow, wrist, hand, foot, etc.

SUMMARY

The various arthroplasty implants, systems, and methods of the present disclosure have been developed in response to the present state of the art, and in particular, in response to the problems and needs in the art that have not yet been fully solved by currently available arthroplasty implants, systems, and methods. In some embodiments, the arthroplasty implants, systems, and methods of the present disclosure may provide improved bone fixation and load sharing between a bone/implant interface under multi-axial and off-loading conditions.

In some embodiments, a bone implant may include a shaft including a proximal end, a distal end, a longitudinal axis, a proximal shaft portion, and a distal shaft portion. The proximal shaft portion may include a first minor diameter and a first helical thread disposed about the proximal shaft portion defining a first major diameter of the proximal shaft portion. The first helical thread may include a first concave undercut surface. The distal shaft portion may include a second minor diameter and a second helical thread disposed about the distal shaft portion defining a second major diameter of the distal shaft portion. The second helical thread may include a second concave undercut surface. The first concave undercut surface and the second concave undercut surface may be angled towards the distal end of the shaft, the second minor diameter of the distal shaft portion may be smaller than the first minor diameter of the proximal shaft portion, and the second major diameter of the distal shaft portion may be smaller than the first major diameter of the proximal shaft portion.

In some embodiments, the bone implant may include a flange component at the proximal end of the shaft. The flange component may include a bone-facing surface and an implement-facing surface.

In some embodiments, the bone-facing surface may include a convex surface.

In some embodiments, the bone-facing surface may include a semi-spherical surface.

In some embodiments, the bone implant may include an attachment feature at the proximal end of the shaft configured to secure an implement.

In some embodiments, the attachment feature may include a post, and the implement may include an articulating head comprising a convex semi-spherical articular surface. The articulating head may be configured to be removably couplable with the post.

In some embodiments, the attachment feature may include a recess, and the implement may include an insert having a concave semi-spherical articular surface. The insert may be configured to be removably couplable with the recess.

In some embodiments, a bone implant may include a shaft, an articulating member disposed at the proximal end of the shaft, and a helical thread. The shaft may include a proximal end, a distal end, a longitudinal axis, a minor diameter, and a threaded shaft portion. The helical thread may be disposed about the shaft defining a length of the threaded shaft portion. The helical thread may include a concave undercut surface angled towards the distal end of the shaft, and a ratio of the length of the threaded shaft portion to the minor diameter of the shaft may be less than 1.50.

In some embodiments, the ratio of the length of the threaded shaft portion to the minor diameter of the shaft may be less than 1.25.

In some embodiments, the ratio of the length of the threaded shaft portion to the minor diameter of the shaft may be less than 1.10.

In some embodiments, the ratio of the length of the threaded shaft portion to the minor diameter of the shaft may be equal to 1.0.

In some embodiments, the ratio of the length of the threaded shaft portion to the minor diameter of the shaft may be less than 1.0.

In some embodiments, the bone implant may include a flange component at the proximal end of the shaft. The flange component may include a bone-facing surface and an implement-facing surface.

In some embodiments, the articulating member may be configured to be removably couplable with an attachment feature at the proximal end of the shaft.

In some embodiments, a shoulder joint implant may include a shaft, a helical thread, and a shoulder joint implement comprising an articular surface at the proximal end of the shaft. The shaft may include a proximal end, a distal end, and a longitudinal axis. The helical thread may be disposed about the shaft along the longitudinal axis between the proximal and distal ends of the shaft. The helical thread may include a first undercut surface, a second undercut surface, a third undercut surface, and a fourth open surface. The first undercut surface and the third undercut surface may be angled towards one of the proximal end and the distal end of the shaft. The second undercut surface and the fourth open surface may be angled towards the other one of the proximal end and the distal end of the shaft.

In some embodiments, the shoulder joint implement may include a glenoid head prosthesis, and the articular surface may include a convex semi-spherical surface.

In some embodiments, the shoulder joint implement may include a humeral head prosthesis, and the articular surface may include a convex semi-spherical surface.

In some embodiments, the shoulder joint implement may include a glenoid insert prosthesis, and the articular surface may include a concave semi-spherical surface.

In some embodiments, the shoulder joint implement may include a humeral insert prosthesis, and the articular surface may include a concave semi-spherical surface.

In some embodiments, the shoulder joint implant may include a flange component at the proximal end of the shaft. The flange component may include a bone-facing surface and an implement-facing surface.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 5C illustrates a bottom view of the bone implant of FIG. 5A; FIG. 5D illustrates a top view of the bone implant of FIG. 5A; FIG. 5E illustrates a side view of the bone implant of FIG. 5A;

FIG. 15 illustrates a side view of the humeral bone of FIG. 14;

FIG. 16 illustrates a cross-sectional side view of the humeral bone of FIG. 15;

Figure 1A:
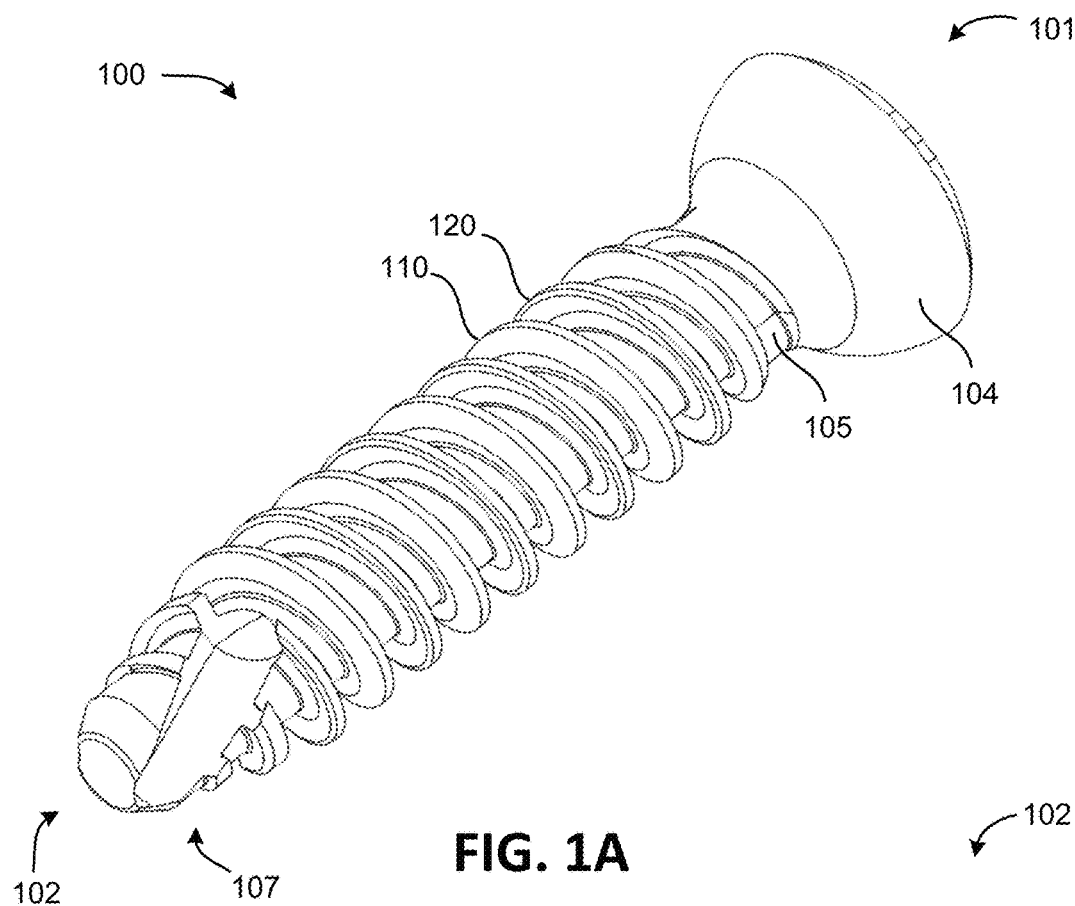
FIG. 1A illustrates a front perspective view of a fastener, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Figure 1B:
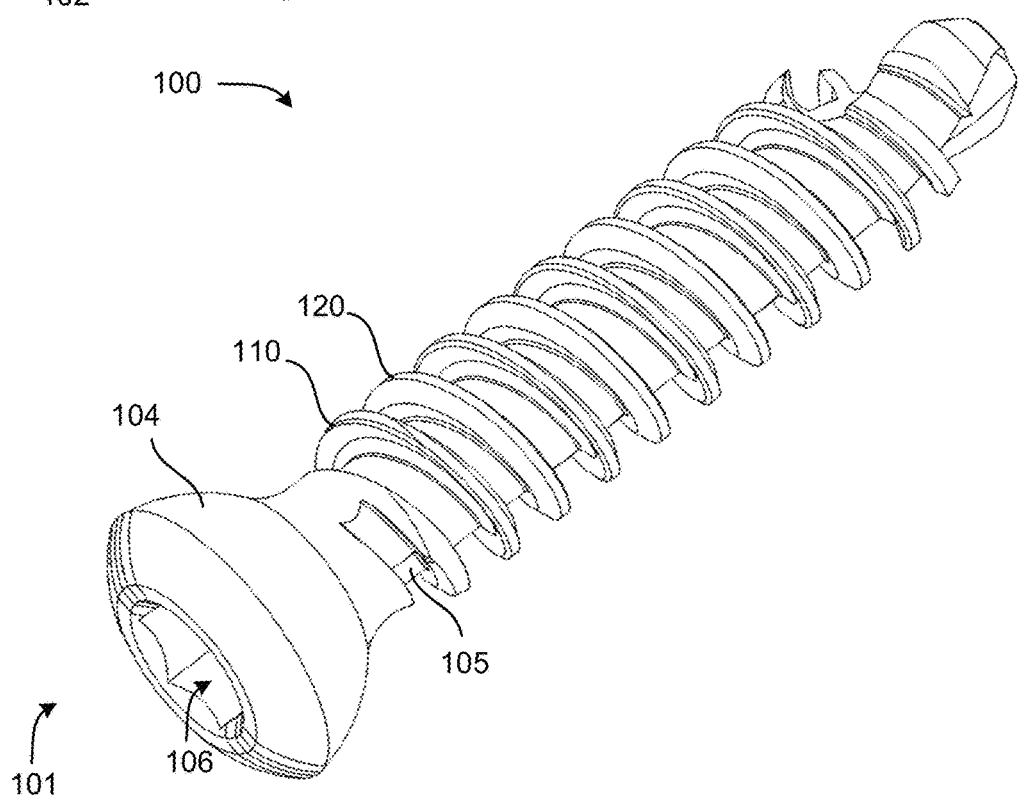
FIG. 1B illustrates a rear perspective view of the fastener of FIG. 1A.
Figure 1C:
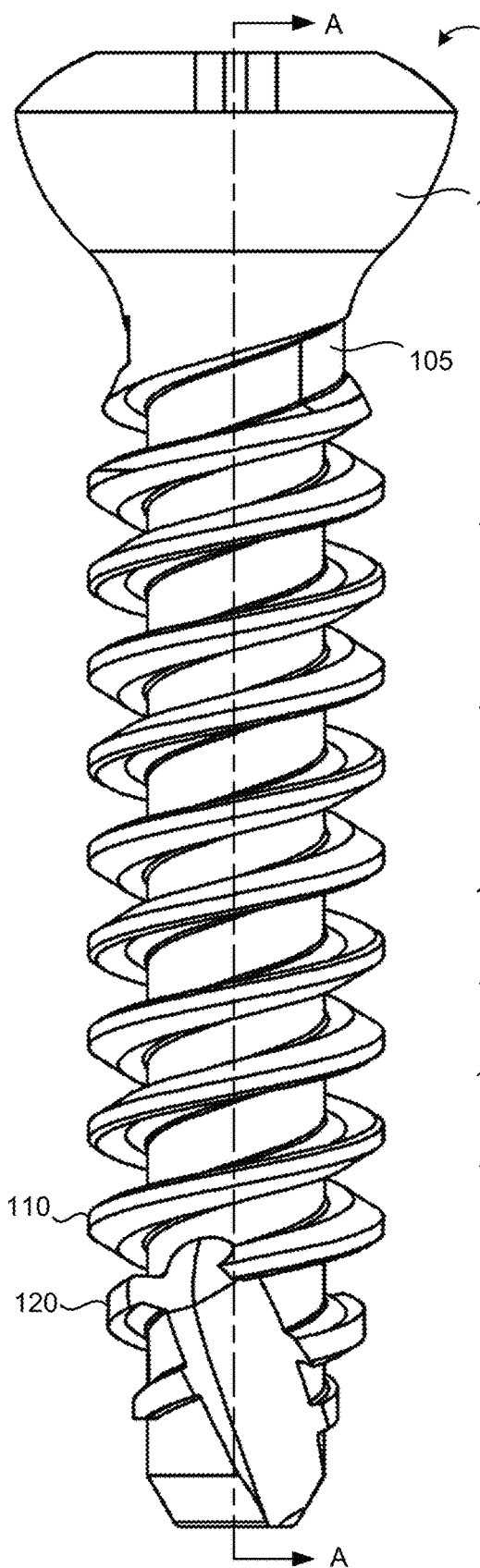
FIG. 1C illustrates a side view of the fastener of FIG. 1A.
Figure 1D:
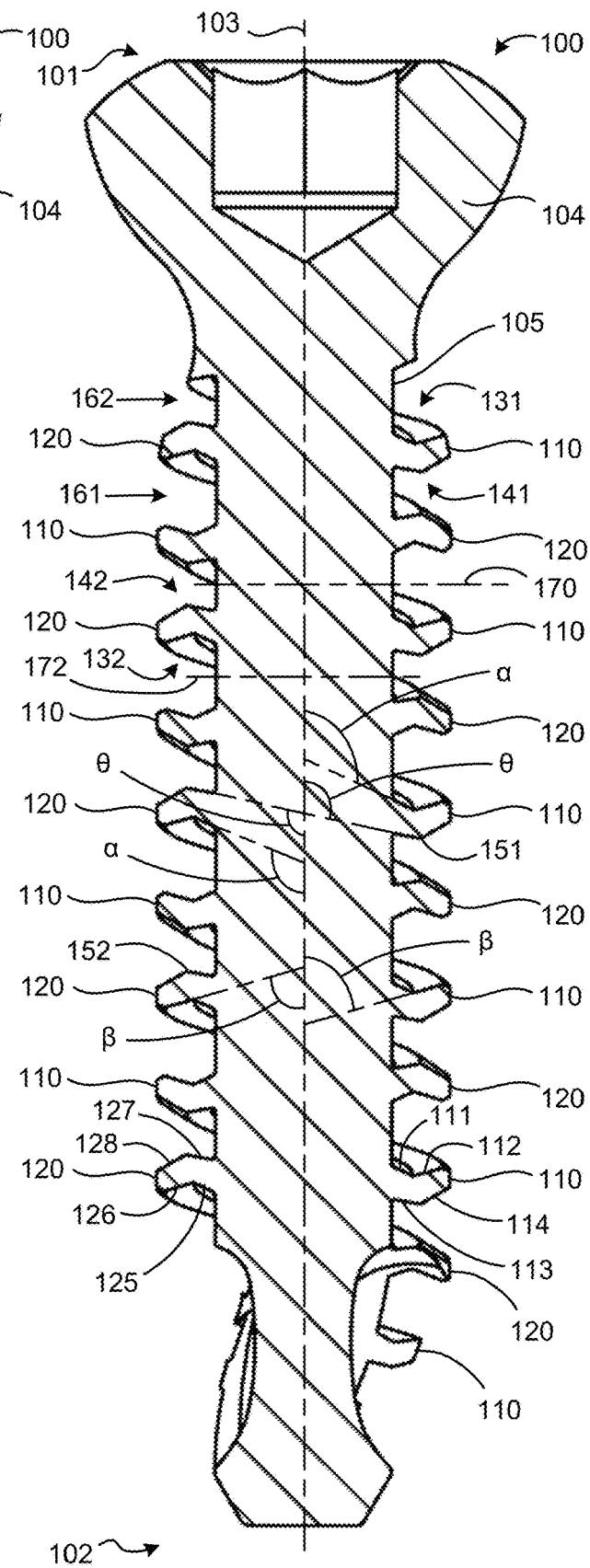
FIG. 1D illustrates a cross-sectional side view of the fastener of FIG. 1A taken along the line A-A shown in FIG. 1C.

FIGS. 1A-1D illustrate various views of a fastener 100, implantable bone anchor, or bone screw, according to one embodiment of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone, as will be discussed in more detail below.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise one or more continuously variable major diameters.

In some embodiments, a thickness of the shaft 105 may vary along a length of the shaft 105 to define one or more minor diameters of the fastener 100, and/or one or more regions along the fastener 100 may comprise one or more continuously variable minor diameters. In some embodiments, a thickness/height/width/length/pitch/angle/shape, etc., of the first helical thread 110 and/or the second helical thread 120 (or any additional helical thread) may vary along a length of the shaft 105. For example, a thickness/height/width/length/pitch/angle/shape, etc., of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105. However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads comprising a "triple start" or "triple lead" thread configuration (not shown).

In some embodiments, the plurality of helical threads may include four helical threads comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100, with the first threading located proximate the distal end of the fastener 100, as well as second threading with any of the shapes disclosed herein oriented toward the other one of the proximal end and the distal end of the fastener 100, with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100 (not shown).

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (e.g., see FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally parallel to each other. The same may be true for the second helical thread 120, in which the second concave undercut surfaces 132 and the second convex undercut surfaces 142 may not have mirror symmetry relative to each other but may be generally parallel to each other.

Conversely, as also shown in FIG. 1D, the proximally-oriented surfaces of the first helical thread 110 may have mirror symmetry relative to the distally-oriented surfaces of the second helical thread 120. Specifically, the first concave undercut surfaces 131 may have mirror symmetry relative to the second convex undercut surfaces 142 about a plane 170 that bisects the space between them and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120 and may also facilitate manufacture of the fastener 100.

Figure 2:
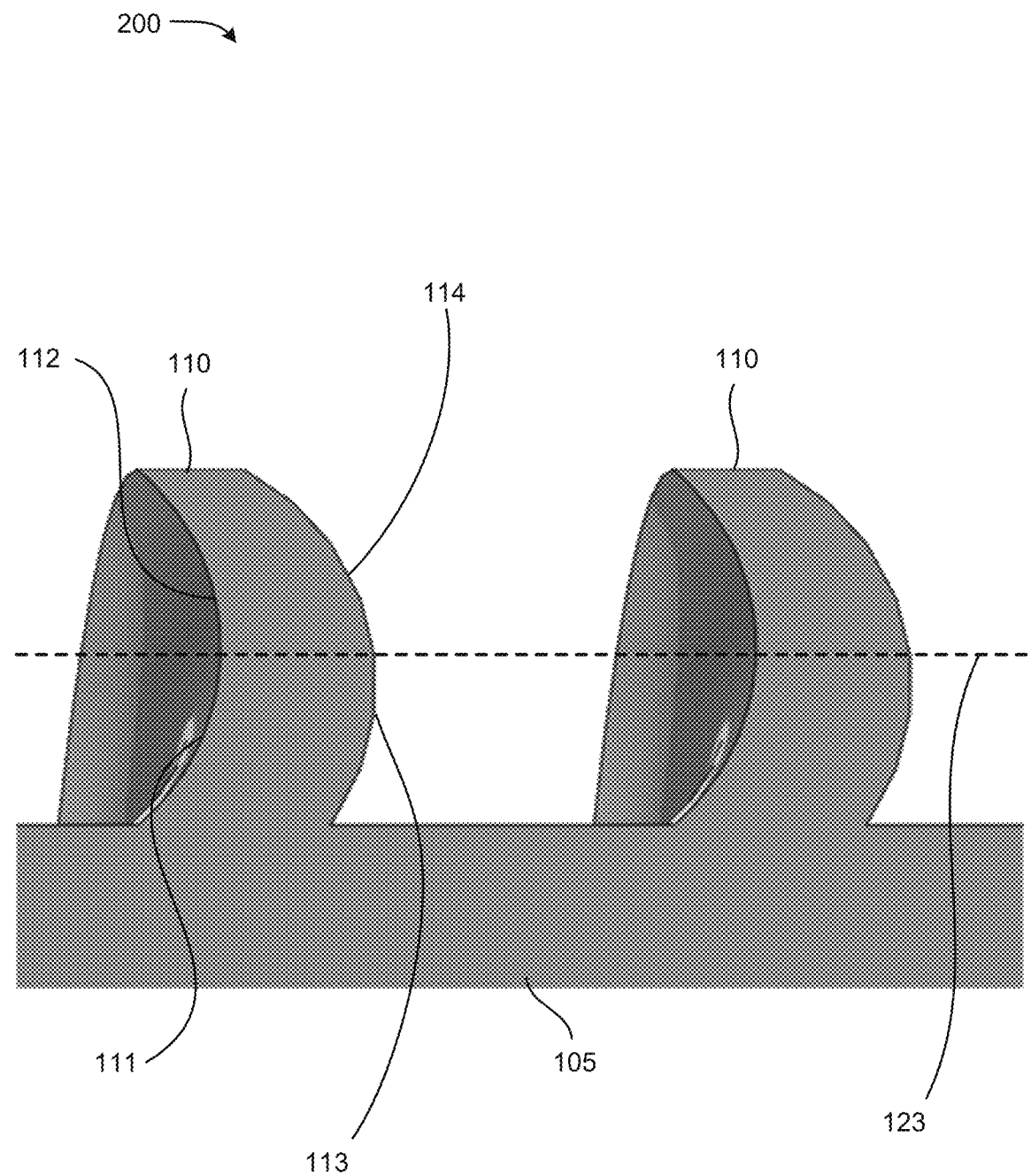
FIG. 2 illustrates a partial cross-sectional side view of a fastener comprising crescent-shaped threading.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 2 illustrates a partial cross-sectional view of a fastener 200 comprising crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, the first helical thread 110 may be bisected by the line 123 shown in FIG. 2 with each crescent shape including a plurality of first undercut surfaces 111, a plurality of second undercut surfaces 112, a plurality of third undercut surfaces 113, and a plurality of fourth open surfaces 114 similar to the helical threading shown in FIG. 1D, except with curved surfaces in place of flat surfaces.

In some embodiments, the plurality of first undercut surfaces 111 and the plurality of second undercut surfaces 112 may comprise concave curved surfaces. However, it will be understood that portions of the plurality of first undercut surfaces 111 and/or portions of the plurality of second undercut surfaces 112 may also comprise convex curved surfaces and/or flat surfaces (not shown in FIG. 2).

In some embodiments, the plurality of third undercut surfaces 113 and the plurality of fourth open surfaces 114 may comprise convex curved surfaces. However, it will be understood that portions of the plurality of third undercut surfaces 113 and the plurality of fourth open surfaces 114 may also comprise concave curved surfaces and/or flat surfaces (not shown in FIG. 2).

In some embodiments, the plurality of third undercut surfaces 113 and the plurality of fourth open surfaces 114 may be replaced by a ramped surface (such as that utilized in a standard buttress thread design) without any undercuts (not shown in FIG. 2). Likewise, any of the other thread designs disclosed herein may utilize a ramped or buttress thread design on at least one side of the helical thread.

In some embodiments, the plurality of first undercut surfaces 111, the plurality of second undercut surfaces 112, the plurality of third undercut surfaces 113, and/or the plurality of fourth open surfaces 114 may comprise a mixture of curved surfaces and flat/faceted surfaces (not shown in FIG. 2). For example, in some embodiments the plurality of first undercut surfaces 111 and the plurality of second undercut surfaces 112 may comprise concave curved surfaces forming a crescent shape, and the plurality of third undercut surfaces 113 and the plurality of fourth open surfaces 114 may comprise flat/faceted surfaces forming a convex undercut surface, similar to the first convex undercut surfaces 141 shown in FIG. 1D.

In some embodiments, a fastener may have only standard threads or only inverted threads. The type of threads that are desired may depend on the type and/or magnitude of loads to be applied to the fastener. For example, a screw loaded axially away from the bone in which it is implanted may advantageously have a standard thread, while a screw loaded axially toward the bone in which it is implanted may advantageously have an inverted thread. A screw that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s), etc., associated with the threading), the major diameter(s), the minor diameter(s), any angulation/angles associated with any surfaces of the threading, the "handedness" of the threading (e.g., right-handed vs. left-handed), etc., may be varied accordingly to suit any specific medium of installation, loading pattern, desired radial loading force, pull-out strength, application, procedure, etc., that may be involved.

In some embodiments, the material(s) of any portion of a fastener described herein may include, but are not limited to metals (e.g., titanium, cobalt, stainless steel, etc.), metal alloys, plastics, polymers, PEEK, UHMWPE, composites, additive particles, textured surfaces, biologics, biomaterials, bone, etc.

In some embodiments, any of the fasteners described herein may include additional features such as: self-tapping features, locking features (e.g., locking threading formed on a portion of the fastener, such as threading located on or near a head of the fastener), cannulation, any style of fastener head (or no fastener head at all), any style of torque connection interface (or no torque connection interface at all), etc.

In some embodiments, a tap (not shown) may be utilized to pre-form threading in a bone according to any threading shape that is disclosed or contemplated herein. In this manner, taps with any suitable shape may be utilized in conjunction with any fastener described or contemplated herein to match or substantially match the threading geometry of a given fastener.

In some embodiments, a minor diameter of the fastener may be selected to match, or substantially match, a diameter of a pilot hole that is formed in a bone to avoid bone blowout when the fastener is inserted into the pilot hole, as will be discussed in more detail below.

Additionally, or alternatively thereto, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include multiple fasteners with any of the different fasteners and thread options described or contemplated herein. The surgeon may select the appropriate fastener(s) from the kit based on the particular loads to be applied and/or the quality of bone in which the fastener(s) are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread 110 may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/other tissues within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle α with respect to the longitudinal axis 103 of the shaft 105, as shown in FIG. 1D.

In some embodiments, the angle α may be greater than 90 degrees.

In some embodiments, the plurality of second undercut surfaces 112 and the plurality of sixth undercut surfaces 126 may each form an angle β with respect to the longitudinal axis 103 of the shaft 105.

In some embodiments, the angle β may be less than 90 degrees.

In some embodiments, the plurality of third undercut surfaces 113 and the plurality of seventh undercut surfaces 127 may each form an angle θ with respect to the longitudinal axis 103 of the shaft 105.

In some embodiments, the angle θ may be approximately 90 degrees.

In some embodiments, the angle θ may be greater than 90 degrees.

It will be understood that the fastener 100 may include any thread configuration, feature, or morphology described or contemplated herein to achieve optimal fixation within a given bone/tissue. Moreover, it will also be understood that the fastener 100 may be utilized in conjunction with (or within) any system, method, or instrumentation described or contemplated herein.

Figure 3A:
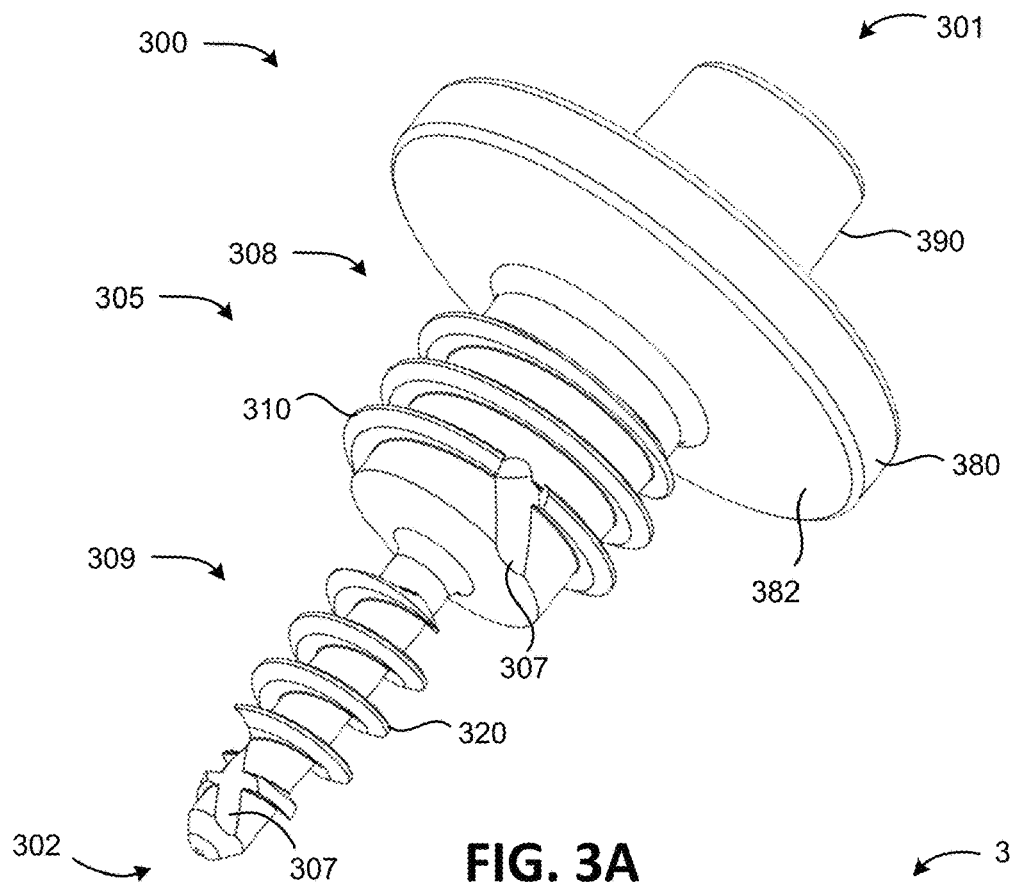
FIG. 3A illustrates a front perspective view of a bone implant, according to an embodiment of the present disclosure.
Figure 3B:
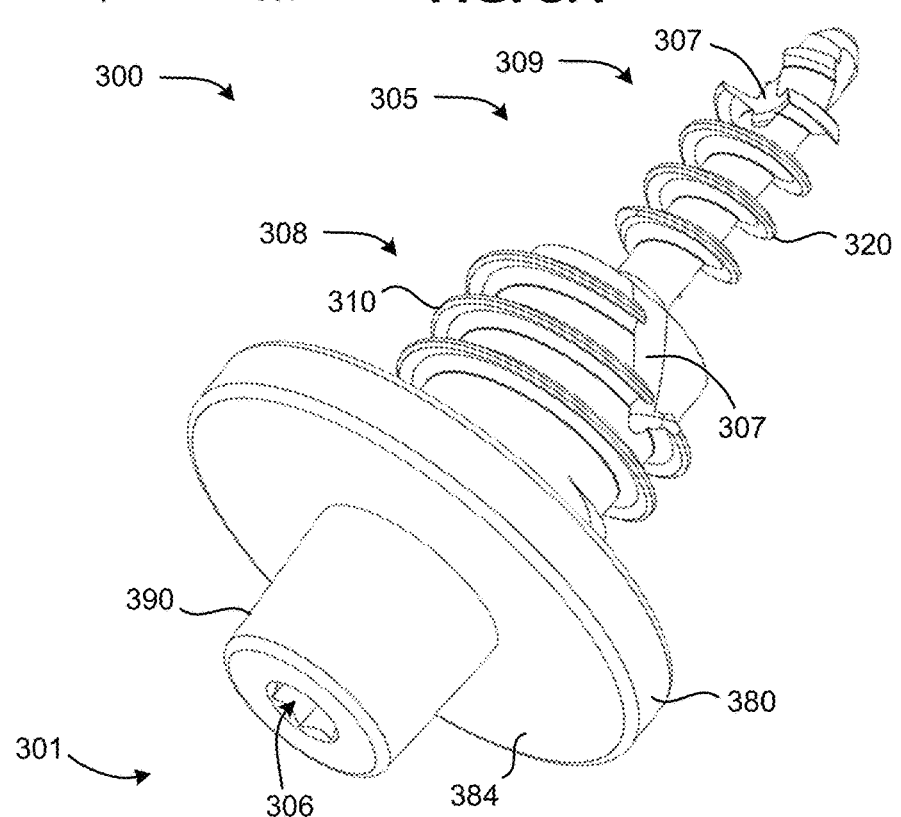
FIG. 3B illustrates a rear perspective view of the bone implant of FIG. 3A.
Figure 3C:
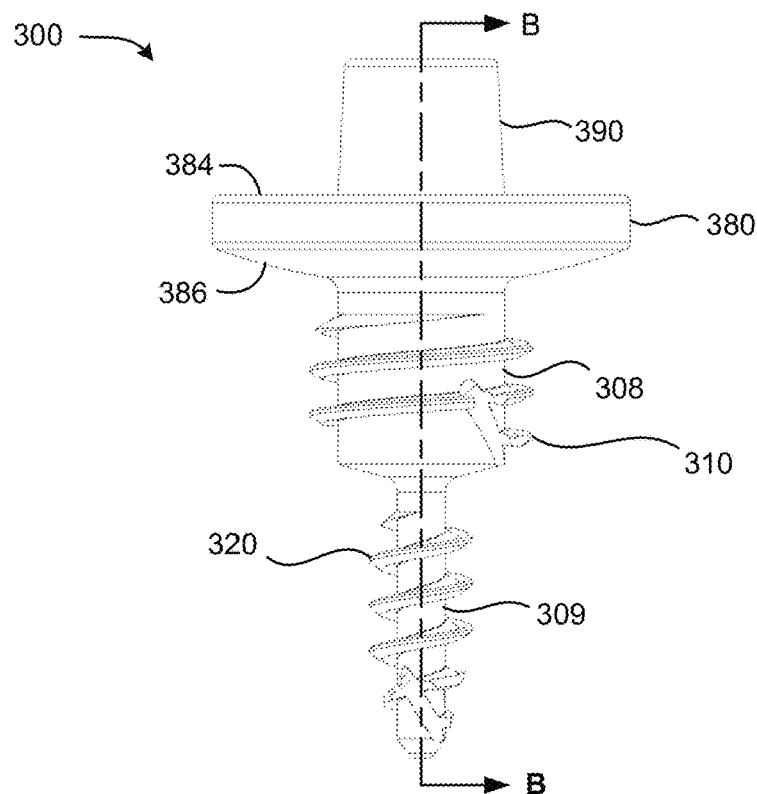
FIG. 3C illustrates a side view of the bone implant of FIG. 3A.
Figure 3D:
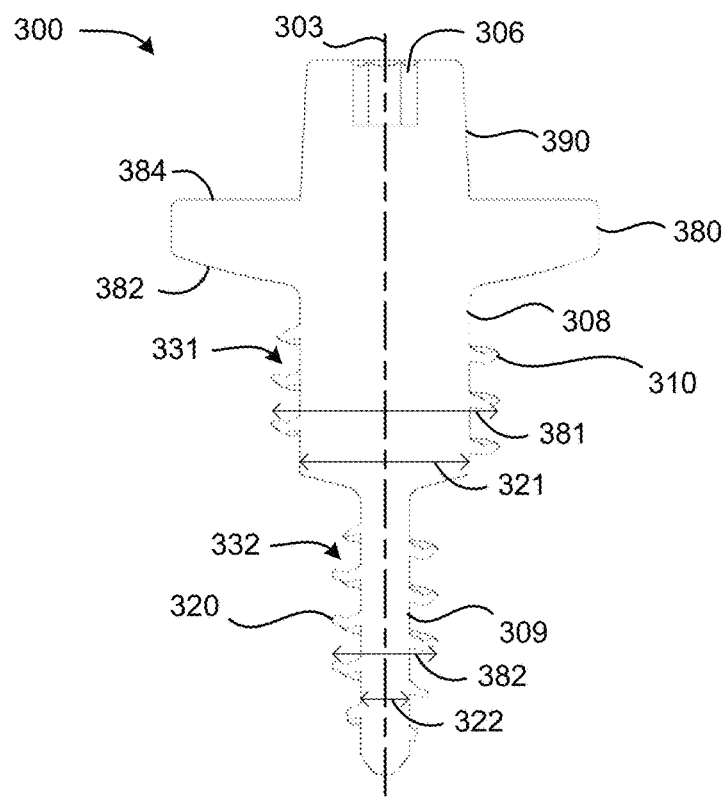
FIG. 3D illustrates a cross-sectional side view of the bone implant of FIG. 3A taken along the line B-B shown in FIG. 3C.

FIGS. 3A-3D illustrate various views of a fastener, implant, shoulder joint implant, or bone implant 300, according to another embodiment of the present disclosure. Specifically, FIG. 3A is a front perspective view of the bone implant 300, FIG. 3B is a rear perspective view of the bone implant 300, FIG. 3C is a side view of the bone implant 300, and FIG. 3D is a cross-sectional side view of the bone implant 300 taken along the line B-B in FIG. 3C.

The bone implant 300 may generally include a shaft 305 having a proximal end 301, a distal end 302, a longitudinal axis 303, a proximal shaft portion 308, a distal shaft portion 309, a first helical thread 310, a second helical thread 320, one or more self-tapping features 307, a flange component 380, an attachment feature or implant post 390, and a torque connection interface 306 formed in/on the implant post 390.

In some embodiments, the proximal shaft portion 308 may have a first minor diameter 321 and a first major diameter 381 defined by the first helical thread 310.

In some embodiments, the distal shaft portion 309 may have a second minor diameter 322 and a second major diameter 382 defined by the second helical thread 320.

In some embodiments, at least a portion of the first minor diameter 321 and/or the second minor diameter 322 may be constant. However, it will also be understood that in some embodiments at least a portion of the first minor diameter 321 and/or the second minor diameter 322 may not be constant.

In some embodiments, at least a portion of the first major diameter 381 and/or the second major diameter 382 may be constant. However, it will also be understood that in some embodiments at least a portion of the first major diameter 381 and/or the second major diameter 382 may not be constant.

In some embodiments, the second minor diameter 322 of the distal shaft portion 309 may be smaller than the first minor diameter 321 of the proximal shaft portion 308.

In some embodiments, the second major diameter 382 of the distal shaft portion 309 may be smaller than the first major diameter 381 of the proximal shaft portion 308.

In some embodiments, the first helical thread 310 may include a first concave undercut surface 331, and the second helical thread 320 may include a second concave undercut surface 332.

In some embodiments, the first concave undercut surface 331 and the second concave undercut surface 332 may be angled towards the distal end 302 of the shaft 305.

However, it will also be understood that the bone implant 300 may include any thread configuration, feature, or morphology described or contemplated herein with respect to any fastener/implant to achieve optimal fixation within a given bone/tissue. For example, in some embodiments the first and second helical threads 310, 320 may comprise standard or inverted threading, a "dual start" thread configuration, etc. Moreover, it will also be understood that the bone implant 300 may be utilized in conjunction with (or within) any system or procedure described or contemplated herein.

In some embodiments, the flange component 380 may be located toward the proximal end of the shaft 305.

In some embodiments, the flange component 380 may include a bone-facing surface 386 and an implement-facing surface 384.

In some embodiments, the bone-facing surface 386 may comprise a convex surface.

In some embodiments, the bone-facing surface 386 may comprise a partial spherical shape.

In some embodiments, the implement-facing surface 384 may comprise a flat circular surface.

In some embodiments, the flange component 380 may include one or more passageways formed therethrough (not shown), similar to the one or more passageways 420 shown in FIGS. 4A-4D.

In some embodiments, the one or more passageways may be configured to receive one or more bone screws therethrough (not shown) and/or promote bone in-growth within the one or more passageways during the healing process.

Figure 21:
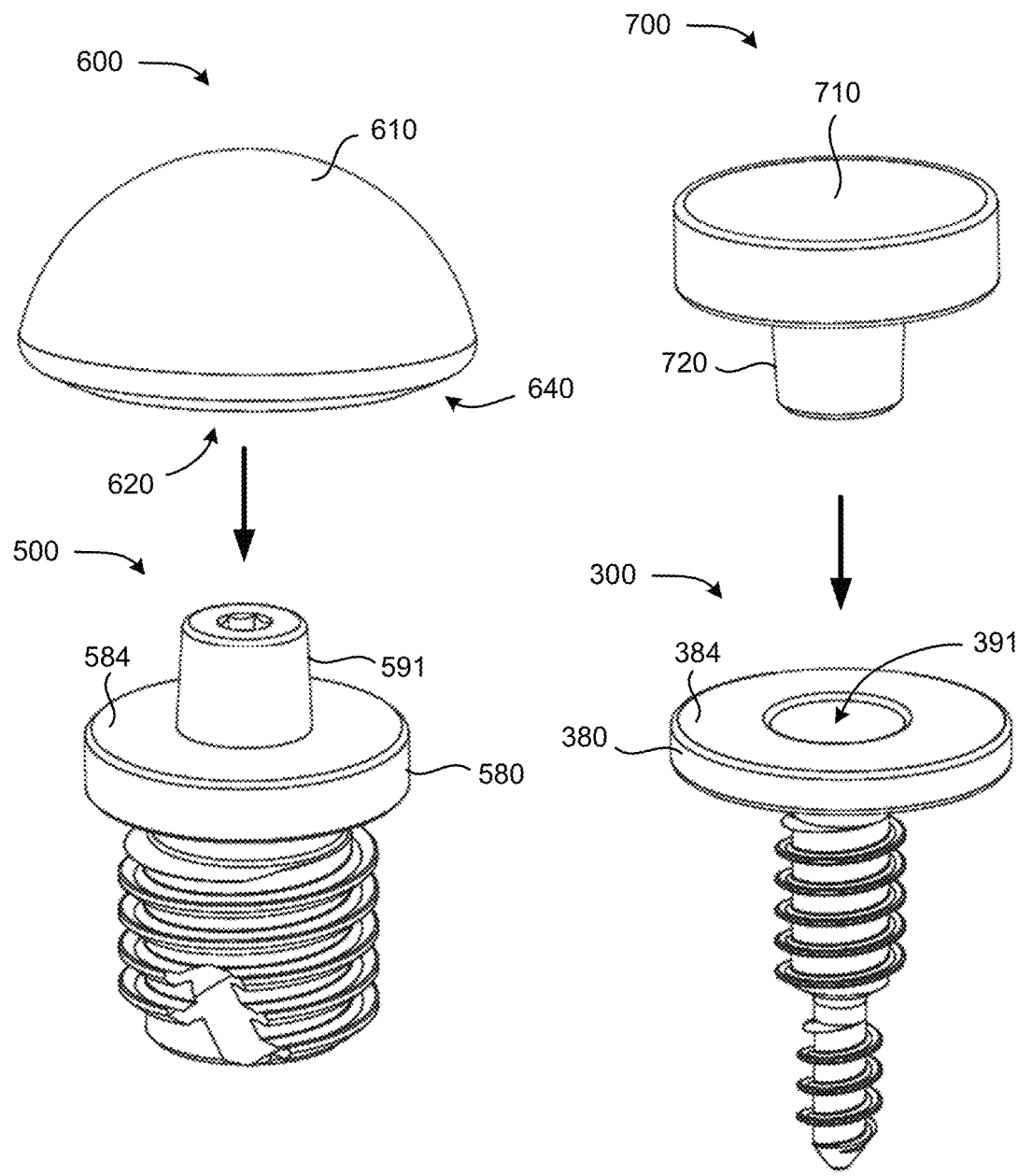
FIG. 21 illustrates a front perspective view of an anatomic shoulder arthroplasty system, according to an embodiment of the present disclosure.

In some embodiments, the attachment feature (e.g., such as the implant post 390, or the implant recess 391 shown in FIG. 21) may be located at the proximal end 301 of the shaft 305 and may be configured to removably secure an implement to the bone implant 300.

In some embodiments, the implant recess 391 (see FIG. 21) may be configured to removably couple with an implement, such as the insert 700 shown in FIGS. 7A and 7B and discussed below in more detail.

In some embodiments, the implant post 390 may be configured to removably couple with an implement, such as the articulating head 600 shown in FIGS. 6A and 6B and discussed below in more detail.

In some embodiments, the implant post 390 may project proximally from the flange component 380.

In some embodiments, the implant post 390 may comprise a cylindrical shape.

In some embodiments, the implant post 390 may comprise a tapered cylindrical shape or a partial conical shape.

In some embodiments, the implant post 390 may comprise a morse taper.

Figure 4A:
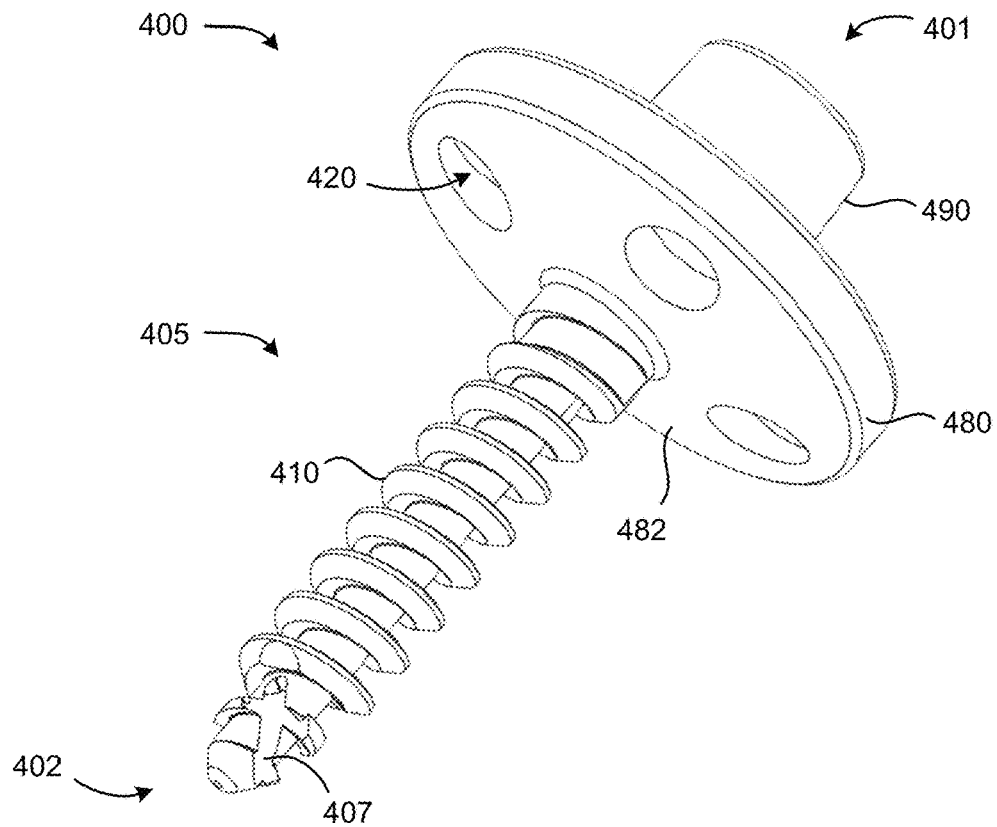
FIG. 4A illustrates a front perspective view of a bone implant, according to another embodiment of the present disclosure.
Figure 4B:
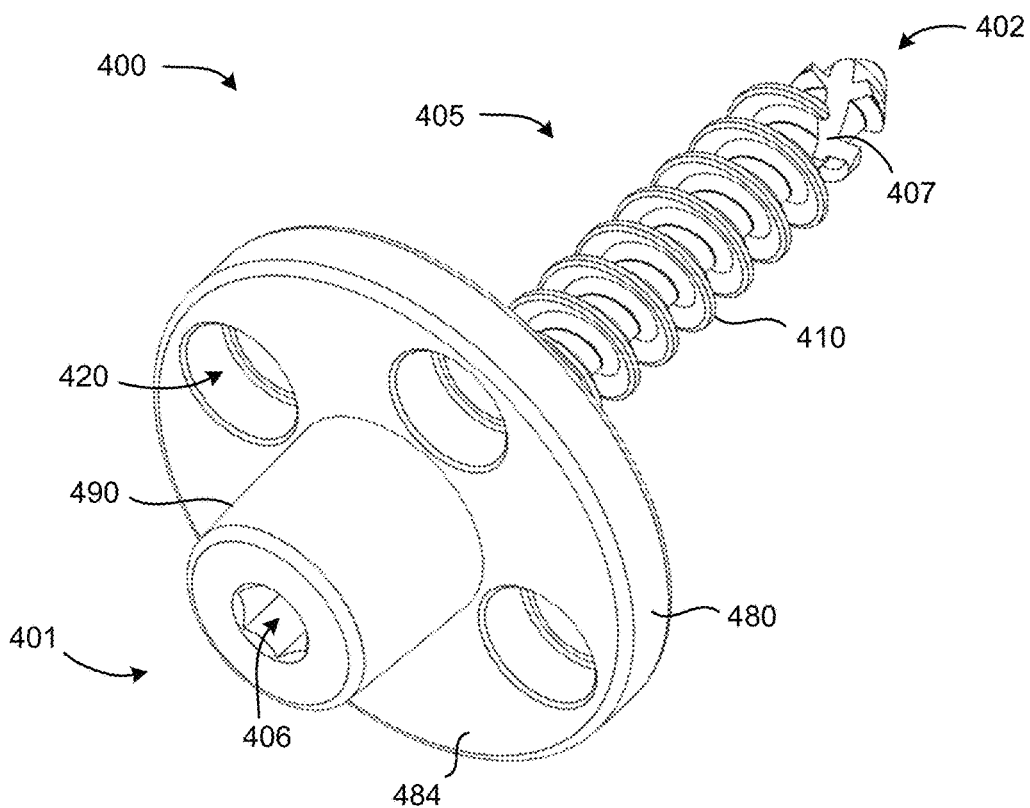
FIG. 4B illustrates a rear perspective view of the bone implant of FIG. 4A.
Figure 4C:
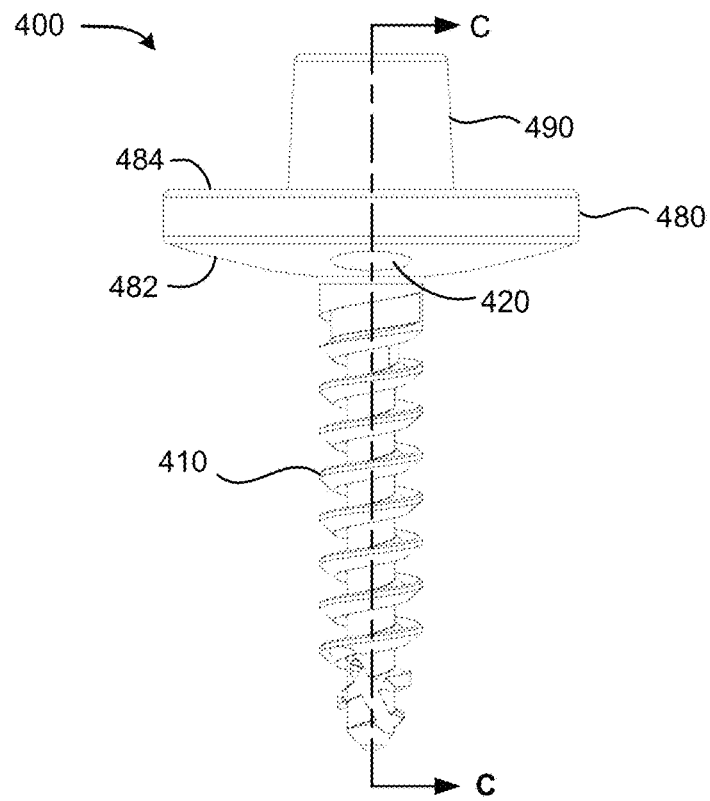
FIG. 4C illustrates a side view of the bone implant of FIG. 4A.
Figure 4D:
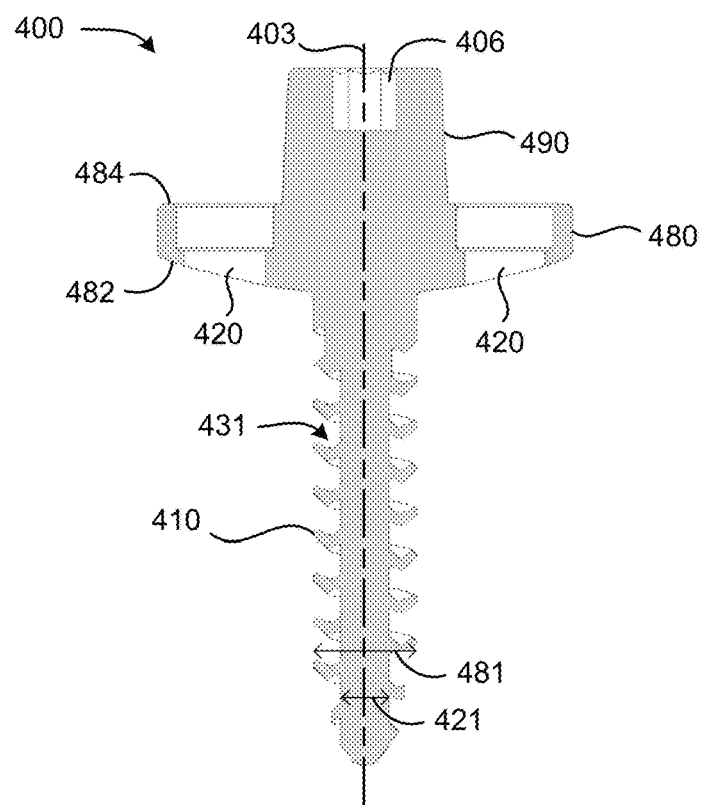
FIG. 4D illustrates a cross-sectional side view of the bone implant of FIG. 4A taken along the line C-C shown in FIG. 4C.

FIGS. 4A-4D illustrate various views of a fastener, implant, shoulder joint implant, or bone implant 400, according to another embodiment of the present disclosure. Specifically, FIG. 4A is a front perspective view of the bone implant 400, FIG. 4B is a rear perspective view of the bone implant 400, FIG. 4C is a side view of the bone implant 400, and FIG. 4D is a cross-sectional side view of the bone implant 400 taken along the line C-C in FIG. 4C.

The bone implant 400 may generally include a shaft 405 having a proximal end 401, a distal end 402, a longitudinal axis 403, a helical thread 410, one or more self-tapping features 407, a flange component 480, an attachment feature or implant post 490, and a torque connection interface 406 formed in/on the implant post 490.

In some embodiments, the shaft 405 may have a minor diameter 421 and a major diameter 481 defined by the helical thread 410.

In some embodiments, at least a portion of the minor diameter 421 may be constant. However, it will also be understood that in some embodiments at least a portion of the minor diameter 421 may not be constant.

In some embodiments, at least a portion of the major diameter 481 may be constant. However, it will also be understood that in some embodiments at least a portion of the major diameter 481 may not be constant.

In some embodiments, the helical thread 410 may include a concave undercut surface 431.

In some embodiments, the concave undercut surface 431 may be angled towards the distal end 402 of the shaft 405.

However, it will also be understood that the bone implant 400 may include any thread configuration, feature, or morphology described or contemplated herein with respect to any fastener/implant to achieve optimal fixation within a given bone/tissue. For example, in some embodiments the helical thread 410 may comprise standard or inverted threading, a "dual start" thread configuration, etc. Moreover, it will also be understood that the bone implant 400 may be utilized in conjunction with (or within) any system or procedure described or contemplated herein.

In some embodiments, the flange component 480 may be located toward the proximal end of the shaft 405.

In some embodiments, the flange component 480 may include a bone-facing surface 482 and an implement-facing surface 484.

In some embodiments, the bone-facing surface 482 may comprise a convex surface.

In some embodiments, the bone-facing surface 482 may comprise a partial spherical shape.

In some embodiments, the implement-facing surface 484 may comprise a flat circular surface.

In some embodiments, the flange component 480 may include one or more passageways 420 formed therethrough.

In some embodiments, the one or more passageways 420 may be configured to receive one or more bone screws therethrough (not shown) and/or promote bone in-growth within the one or more passageways 420 during the healing process.

Figure 7A:
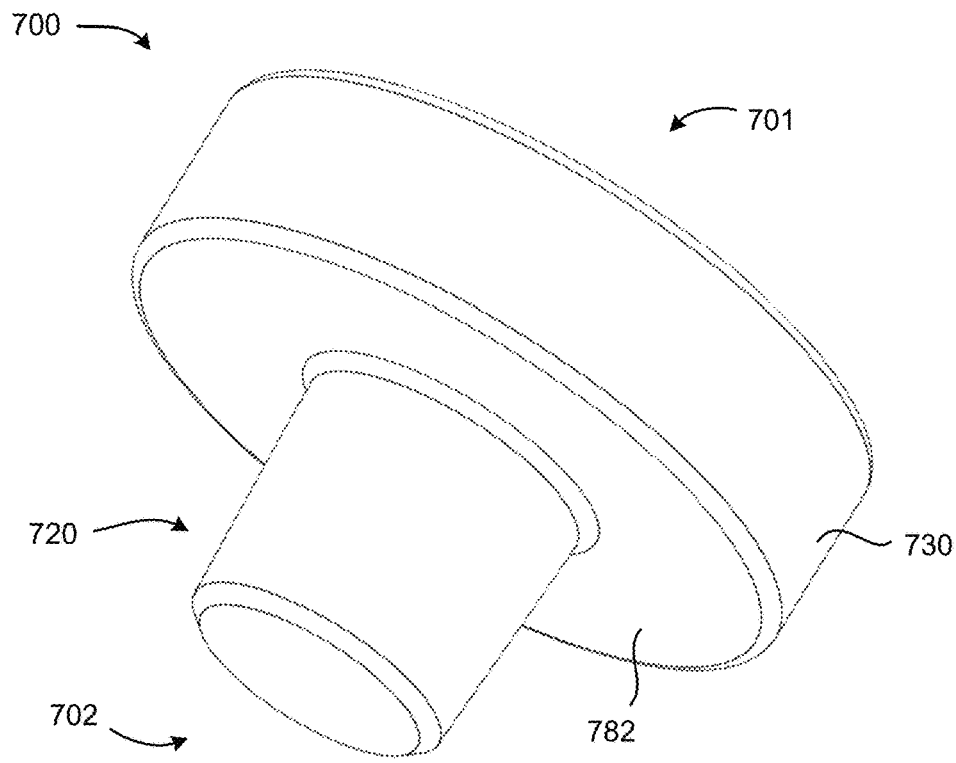
FIG. 7A illustrates a bottom perspective view of an implement, according to another embodiment of the present disclosure.
Figure 7B:
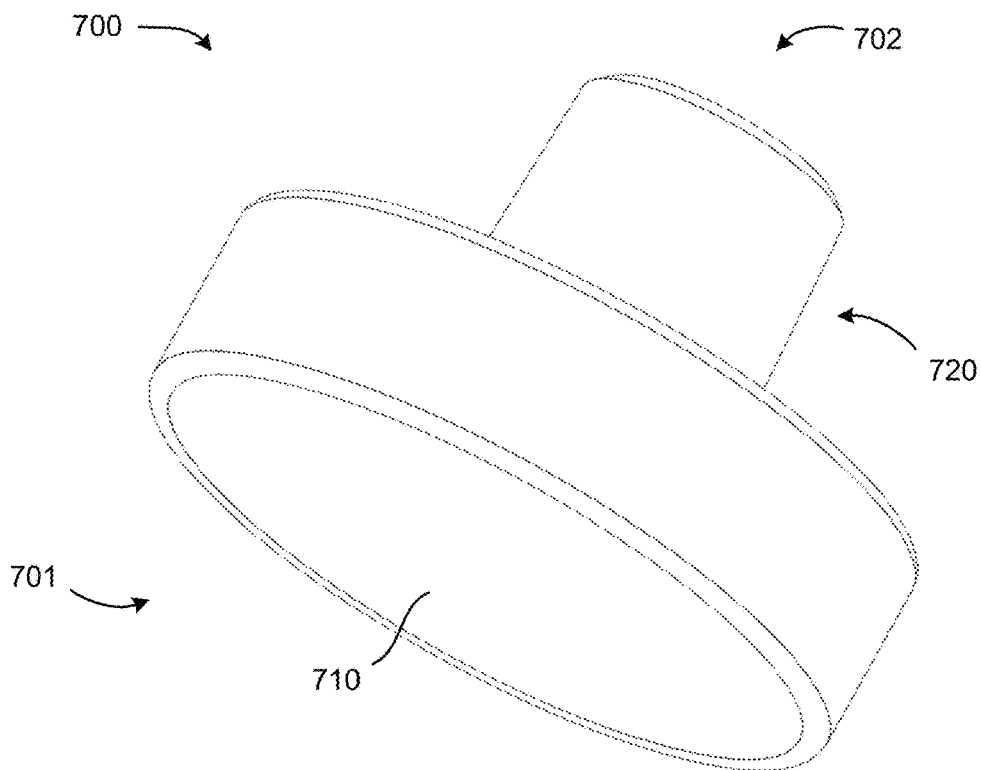
FIG. 7B illustrates a top perspective view of the implement of FIG. 7A.
Figure 20:
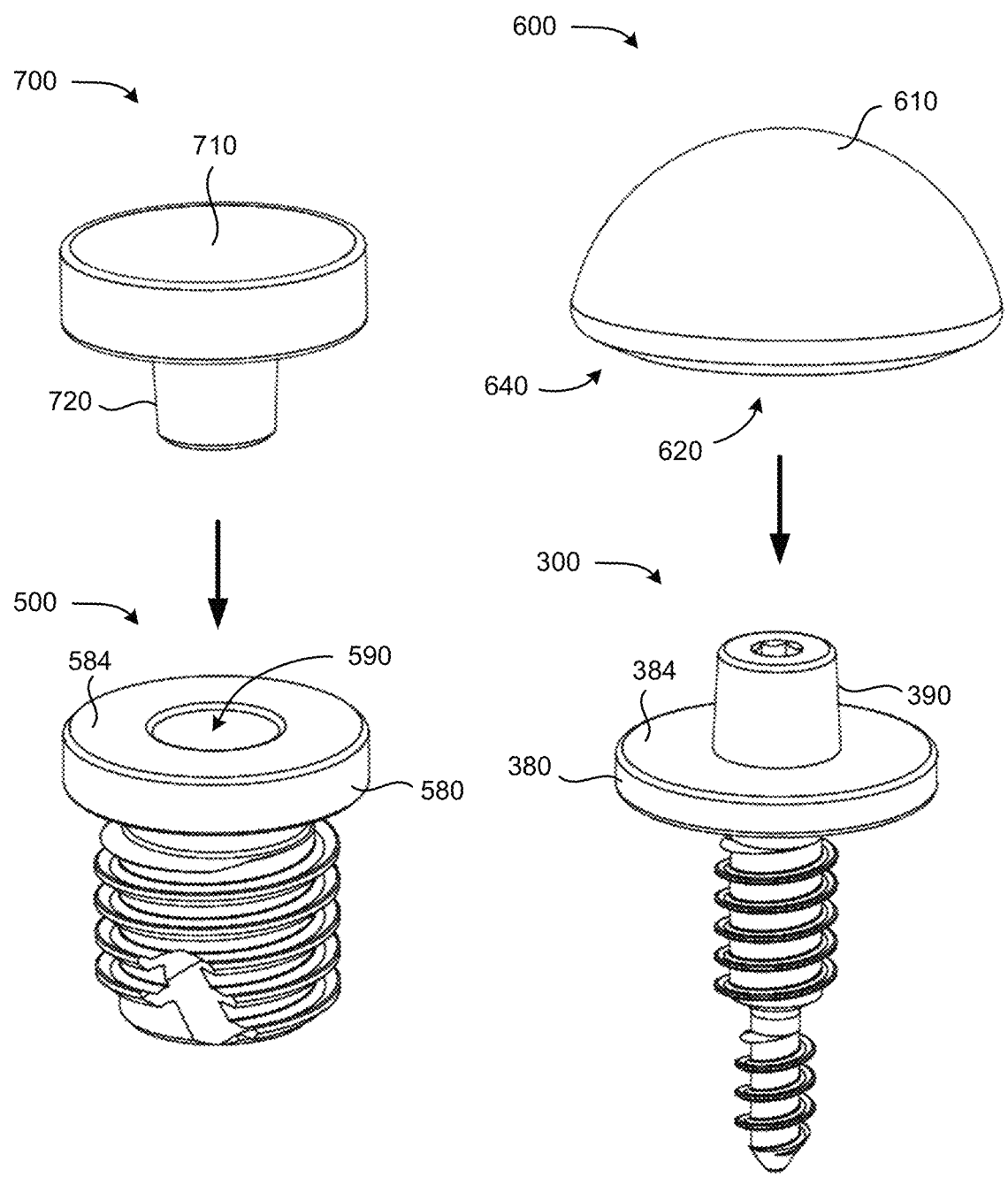
FIG. 20 illustrates a front perspective view of a reverse shoulder arthroplasty system, according to an embodiment of the present disclosure.

In some embodiments, the attachment feature (e.g., such as the implant post 490, or alternatively an implant recess (not shown) similar to the implant recess 590 shown in FIG. 20) may be located at the proximal end 401 of the shaft 405 and may be configured to removably secure an implement to the bone implant 400, such as the insert 700 shown in FIGS. 7A and 7B.

Figure 6A:
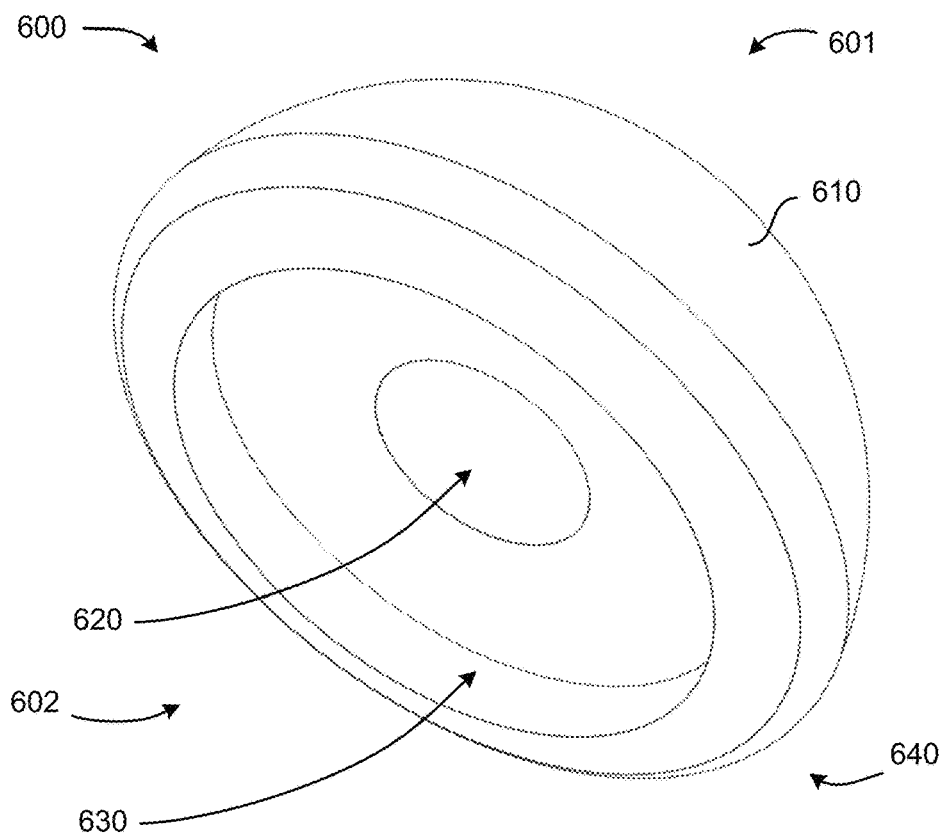
FIG. 6A illustrates a perspective view of an implement, according to an embodiment of the present disclosure.
Figure 6B:
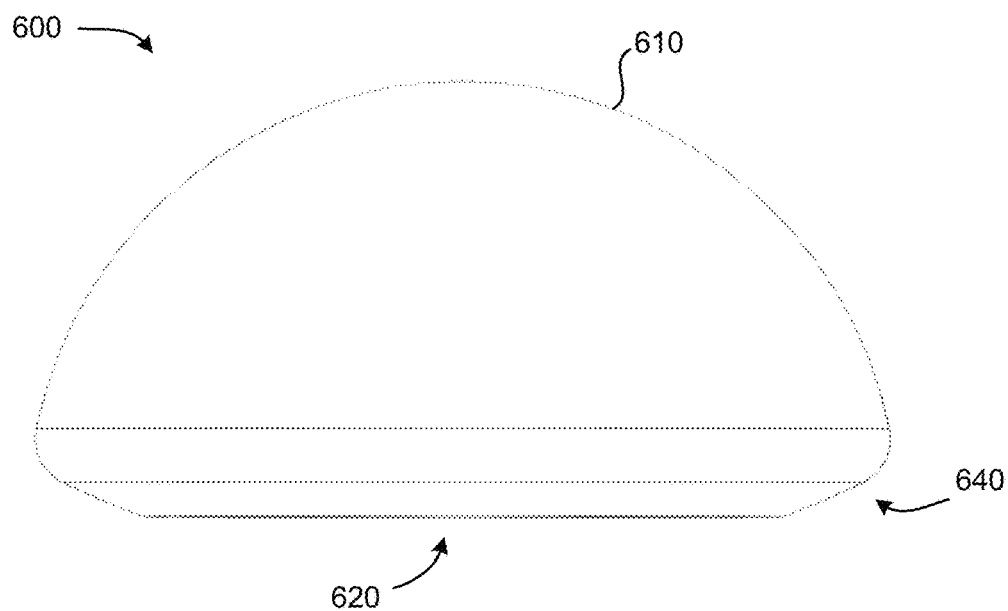
FIG. 6B illustrates a side view of the implement of FIG. 6A.

In some embodiments, the implant post 490 may be configured to removably couple with an implement, such as the articulating head 600 shown in FIGS. 6A and 6B.

In some embodiments, the implant post 490 may project proximally from the flange component 480.

In some embodiments, the implant post 490 may comprise a cylindrical shape.

In some embodiments, the implant post 490 may comprise a tapered cylindrical shape or a partial conical shape.

In some embodiments, the implant post 490 may comprise a morse taper.

Figure 5A:
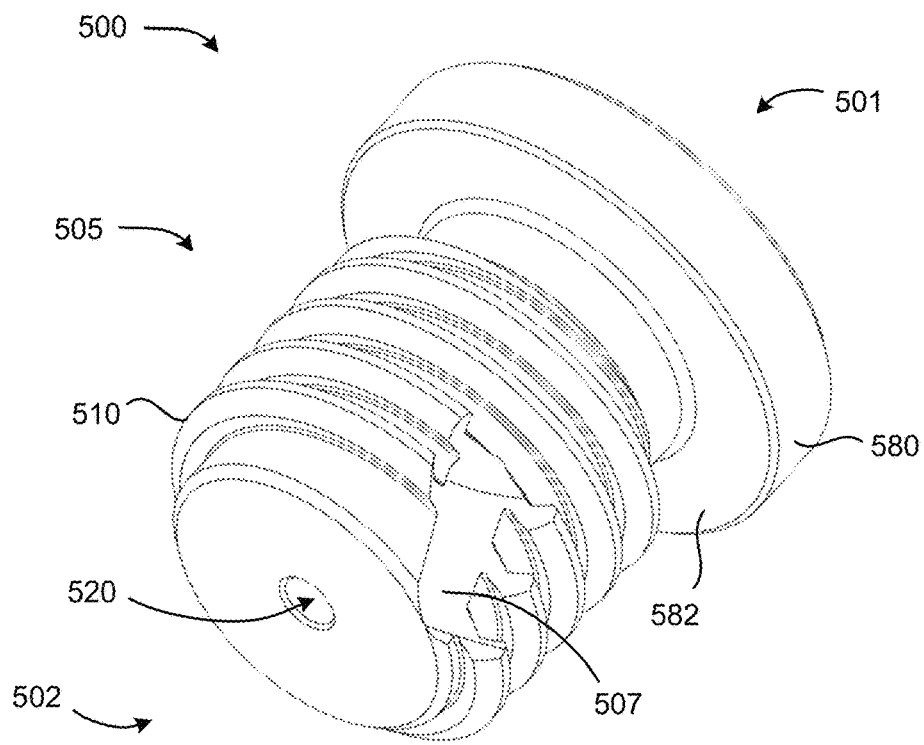
FIG. 5A illustrates a front perspective view of a bone implant, according to another embodiment of the present disclosure.
Figure 5B:
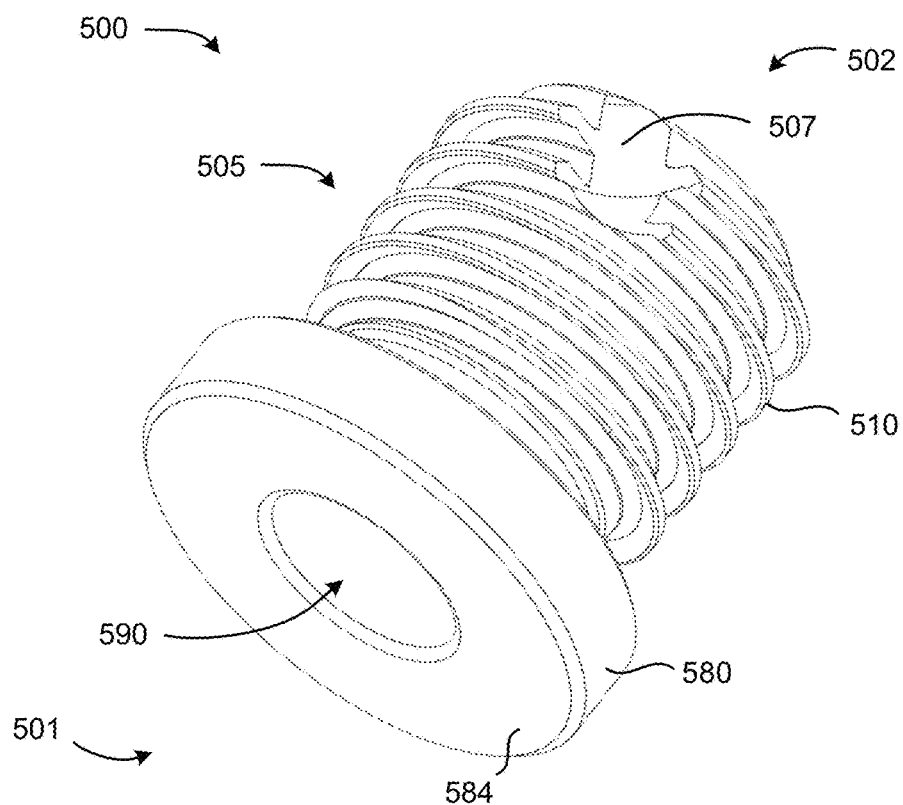
FIG. 5B illustrates a rear perspective view of the bone implant of FIG. 5A.

FIGS. 5A-5E illustrate various views of a fastener, implant, shoulder joint implant, or bone implant 500, according to another embodiment of the present disclosure. Specifically, FIG. 5A is a front perspective view of the bone implant 500, FIG. 5B is a rear perspective view of the bone implant 500, FIG. 5C is a bottom view of the bone implant 500, FIG. 5D is a top view of the bone implant 500, and FIG. 5E is a side view of the bone implant 500.

The bone implant 500 may generally include a shaft 505 having a proximal end 501, a distal end 502, a longitudinal axis 503, a helical thread 510, one or more self-tapping features 507, a flange component 580, an attachment feature or implant recess 590, and a central longitudinal passageway 520.

In some embodiments, the shaft 505 may have a minor diameter 521 and a major diameter 581 defined by the helical thread 510.

In some embodiments, at least a portion of the minor diameter 521 may be constant. However, it will also be understood that in some embodiments at least a portion of the minor diameter 521 may not be constant.

In some embodiments, at least a portion of the major diameter 581 may be constant. However, it will also be understood that in some embodiments at least a portion of the major diameter 581 may not be constant.

In some embodiments, the helical thread 510 may include a concave undercut surface 531.

In some embodiments, the concave undercut surface 531 may be angled towards the distal end 502 of the shaft 505.

However, it will also be understood that the bone implant 500 may include any thread configuration, feature, or morphology described or contemplated herein with respect to any fastener/implant to achieve optimal fixation within a given bone/tissue. For example, in some embodiments the helical thread 510 may comprise standard or inverted threading, a "dual start" thread configuration, etc. Moreover, it will also be understood that the bone implant 500 may be utilized in conjunction with (or within) any system or procedure described or contemplated herein.

In some embodiments, the helical thread 510 disposed about the shaft 505 may define a threaded shaft portion 515 along a length of the shaft 505.

In some embodiments, a ratio of the length of the threaded shaft portion 515 to the minor diameter 521 of the shaft 505 may be less than 1.50.

In some embodiments, a ratio of the length of the threaded shaft portion 515 to the minor diameter 521 of the shaft 505 may be less than 1.25.

In some embodiments, a ratio of the length of the threaded shaft portion 515 to the minor diameter 521 of the shaft 505 may be less than 1.10.

In some embodiments, a ratio of the length of the threaded shaft portion 515 to the minor diameter 521 of the shaft 505 may be equal to 1.0.

In some embodiments, a ratio of the length of the threaded shaft portion 515 to the minor diameter 521 of the shaft 505 may be less than 1.0.

In some embodiments, the flange component 580 may be located toward the proximal end of the shaft 505.

In some embodiments, the flange component 580 may include a bone-facing surface 582 and an implement-facing surface 584.

In some embodiments, the bone-facing surface 582 and/or the implement-facing surface 584 may each comprise a flat circular surface. However, it will also be understood that in some embodiments the bone-facing surface 582 and/or the implement-facing surface 584 may comprise convex surfaces, concave surfaces, partial spherical surfaces, etc.

In some embodiments, the flange component 580 may be integrally formed with the shaft 505. However, it will also be understood that the flange component 580 may be coupled to the shaft 505 via any suitable method including, but not limited to, a morse taper, a set screw, a tab, a locking element, etc., (not shown), without departing from the spirit or scope of the present disclosure.

In some embodiments, the attachment feature (e.g., such as the implant recess 590, or alternatively the implant post 591 shown in FIG. 21) may be located at the proximal end 501 of the shaft 505 and may be configured to removably secure an implement or articulating member to the bone implant 500.

In some embodiments, the implant recess 590 may be configured to removably couple with an articulating member, such as the insert 700 shown in FIGS. 7A and 7B.

In some embodiments, the implant post 591 may be configured to removably couple with an articulating member, such as the articulating head 600 shown in FIGS. 6A and 6B.

In some embodiments, the implant post 591 may project proximally from the flange component 580.

In some embodiments, the implant post 591 may comprise a cylindrical shape.

In some embodiments, the implant post 591 may comprise a tapered cylindrical shape or a partial conical shape.

In some embodiments, the implant post 591 may comprise a morse taper.

FIGS. 6A and 6B illustrate a perspective view and a side view of an implement, shoulder joint implement, articulating member, or articulating head 600, according to an embodiment of the present disclosure.

The articulating head 600 may generally include a proximal end 601, a distal end 602, a convex articular surface 610, a post recess 620, a flange component recess 630, and a beveled surface 640.

Figure 19:
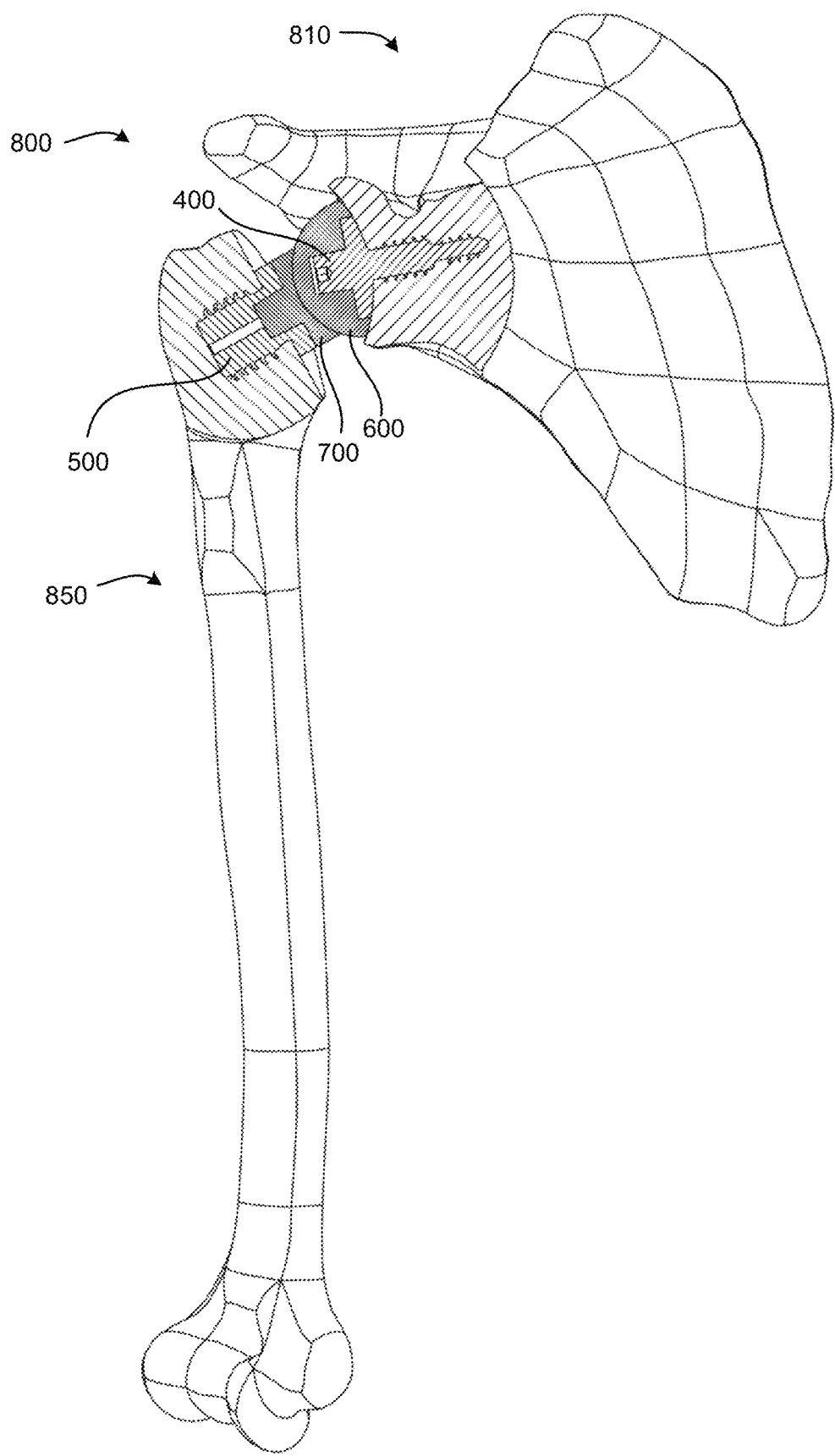
FIG. 19 illustrates a cross-sectional side view of the shoulder joint shown in FIG. 18.

In some embodiments, the articulating head 600 may comprise a glenoid head prosthesis which may be utilized in a reverse shoulder arthroplasty system (e.g., see articulating head 600 shown in FIGS. 19 and 20).

In some embodiments, the articulating head 600 may comprise a humeral head prosthesis which may be utilized in an anatomic shoulder arthroplasty (e.g., see articulating head 600 shown in FIG. 21).

In some embodiments, the convex articular surface 610 may comprise a convex semi-spherical articular surface.

In some embodiments, the convex articular surface 610 of the articulating head 600 may be received within, and/or articulate against, the concave articular surface 710 of the insert 700 shown in FIGS. 7A and 7B.

In some embodiments, the post recess 620 formed in the articulating head 600 may be shaped and configured to removably couple with the implant posts of the bone implants previously discussed herein.

In some embodiments, the post recess 620 may comprise a cylindrical shape.

In some embodiments, the post recess 620 may comprise a tapered cylindrical shape or a partial conical shape.

In some embodiments, the post recess 620 may comprise a morse taper.

In some embodiments, the flange component recess 630 formed in the distal end 602 of the articulating head 600 may be shaped and configured to removably couple with the flange components of the bone implants previously discussed herein.

FIGS. 7A and 7B illustrate bottom and top perspective views of an implement, shoulder joint implement, articulating member, or insert 700, according to an embodiment of the present disclosure.

The insert 700 may generally include a proximal end 701, a distal end 702, a concave articular surface 710, an outer surface 730, an implant-facing surface 782, and an insert post 720.

In some embodiments, the insert 700 may comprise a glenoid insert prosthesis which may be utilized in a reverse shoulder arthroplasty system (e.g., see insert 700 shown in FIGS. 19 and 20).

In some embodiments, the insert 700 may comprise a humeral insert prosthesis which may be utilized in an anatomic shoulder arthroplasty (e.g., see insert 700 shown in FIG. 21).

In some embodiments, the concave articular surface 710 may comprise a concave semi-spherical articular surface.

In some embodiments, the concave articular surface 710 of the insert 700 may receive, and/or articulate against, the convex articular surface 610 of the articulating head 600 shown in FIGS. 6A and 6B.

In some embodiments, the insert post 720 of the insert 700 may be shaped and configured to removably couple with the implant recesses of the bone implants previously discussed herein.

In some embodiments, the insert post 720 may comprise a cylindrical shape.

In some embodiments, the insert post 720 may comprise a tapered cylindrical shape or a partial conical shape.

In some embodiments, the insert post 720 may comprise a morse taper.

Figure 8:
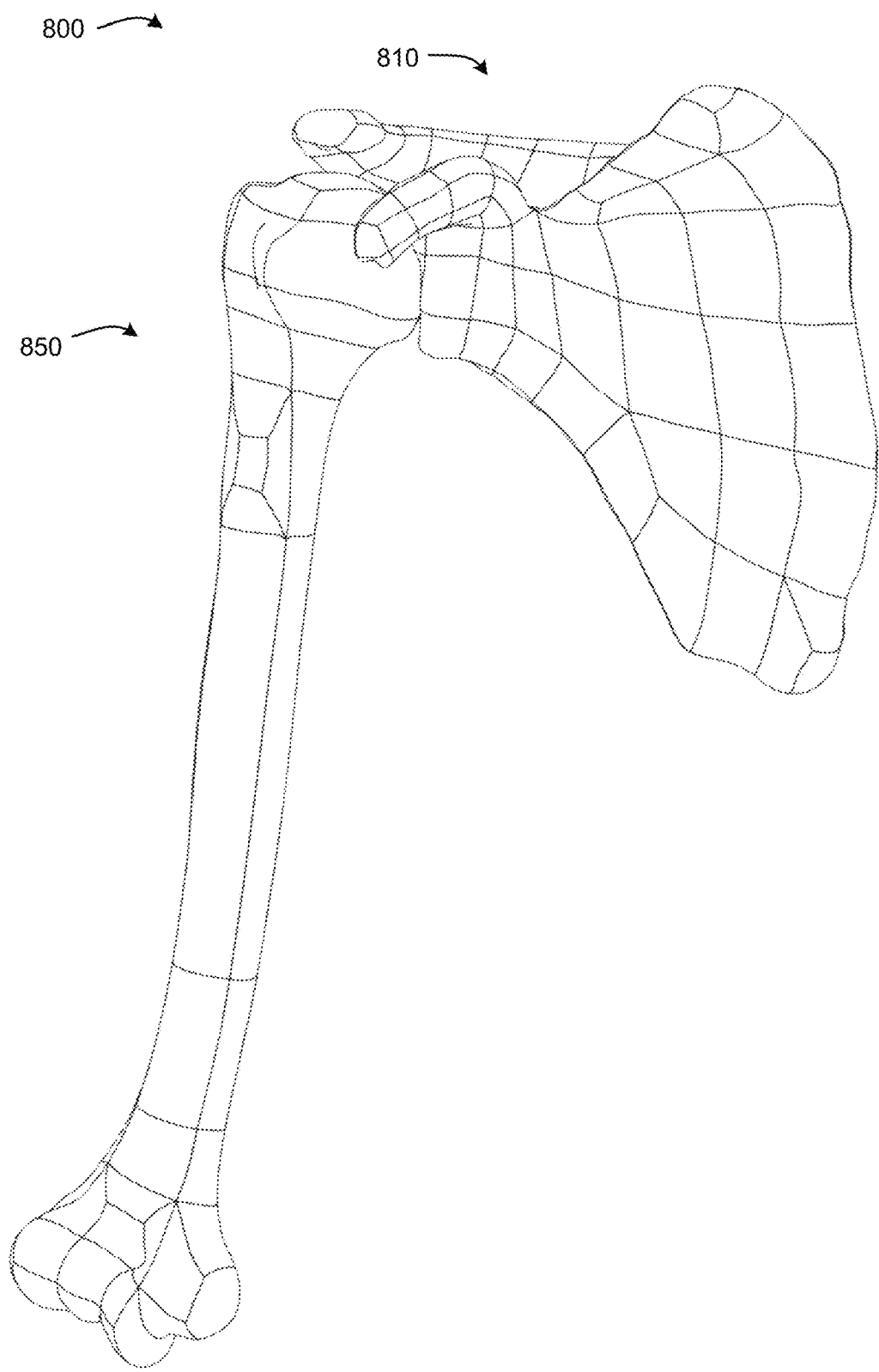
FIG. 8 illustrates a front view of a shoulder joint, according to an embodiment of the present disclosure.
Figure 17:
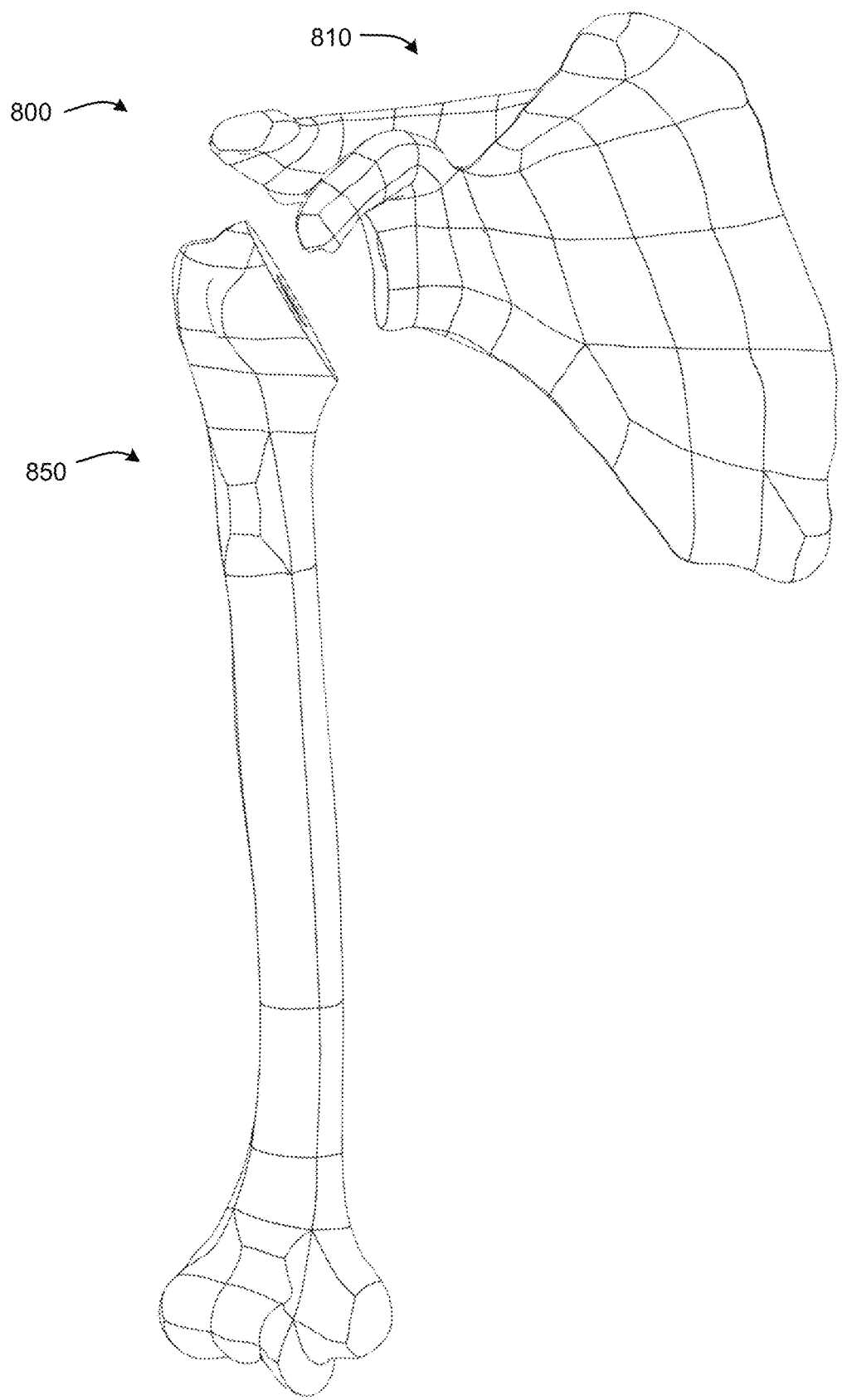
FIG. 17 illustrates a front view of the shoulder joint of FIG. 8 with prepared humeral and scapula bones prior to receiving one or more shoulder joint implants.
Figure 18:
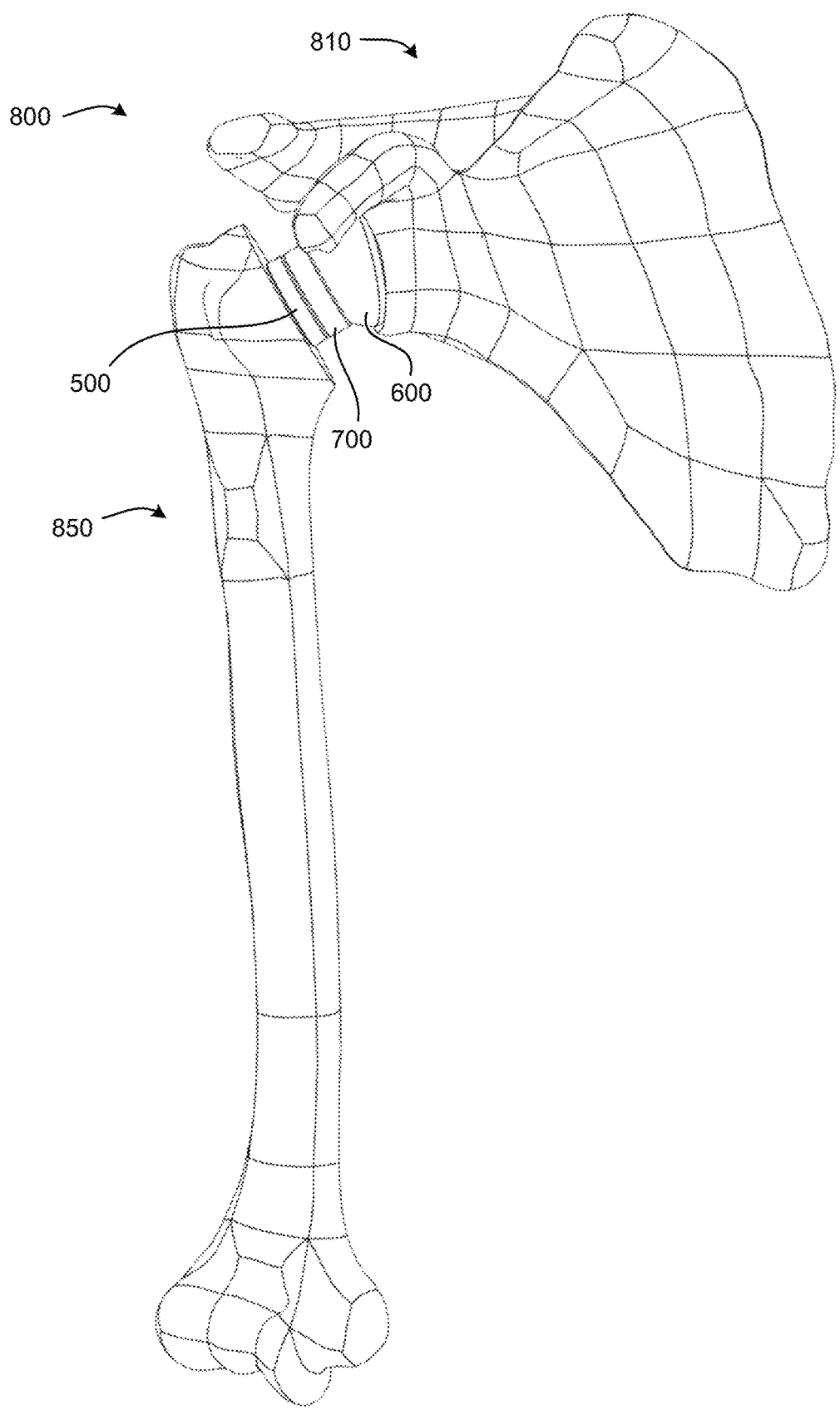
FIG. 18 illustrates a front view of the shoulder joint of FIG. 17 with a reverse shoulder arthroplasty system.

FIGS. 8-19 illustrate an example shoulder arthroplasty procedure, according to an embodiment of the present disclosure. Specifically, FIG. 8 is a front view of a shoulder joint 800 comprising a scapula bone 810 and a humeral bone 850, FIGS. 9-12 illustrate preparation of the scapula bone 810, FIGS. 13-16 illustrate preparation of the humeral bone 850, FIG. 17 is a front view of the prepared shoulder joint 800, FIG. 18 is a front view of the shoulder joint 800 with a reverse shoulder arthroplasty system installed therein, and FIG. 19 is a cross-sectional side view of FIG. 18.

Figure 9:
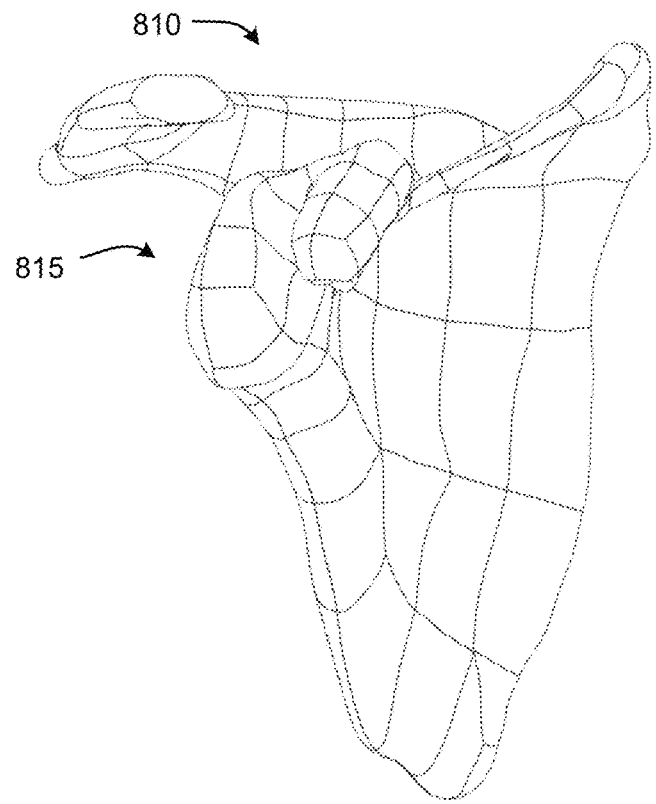
FIG. 9 illustrates a perspective view of a scapula bone of the shoulder joint of FIG. 8.
Figure 10:
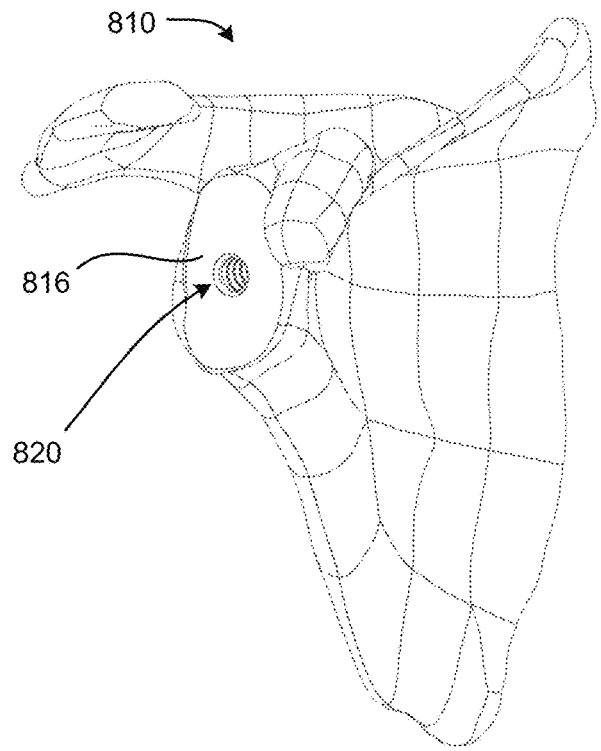
FIG. 10 illustrates the scapula bone of FIG. 9 with a prepared glenoid.
Figure 11:
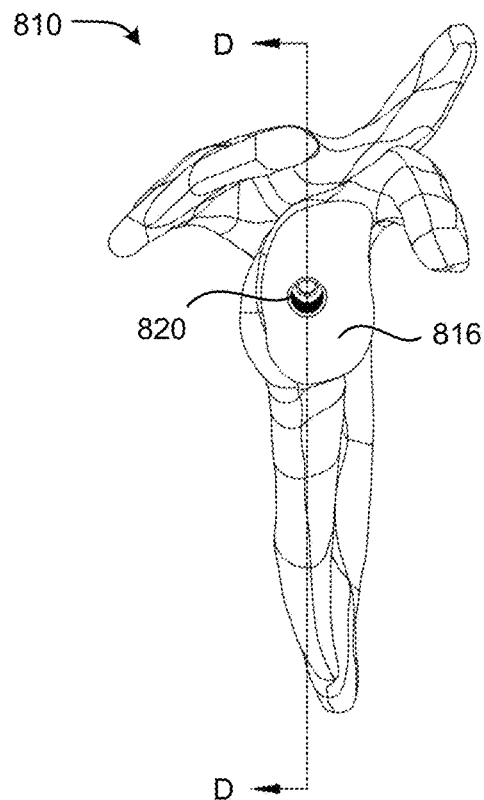
FIG. 11 illustrates a side view of the scapula bone of FIG. 10.
Figure 12:
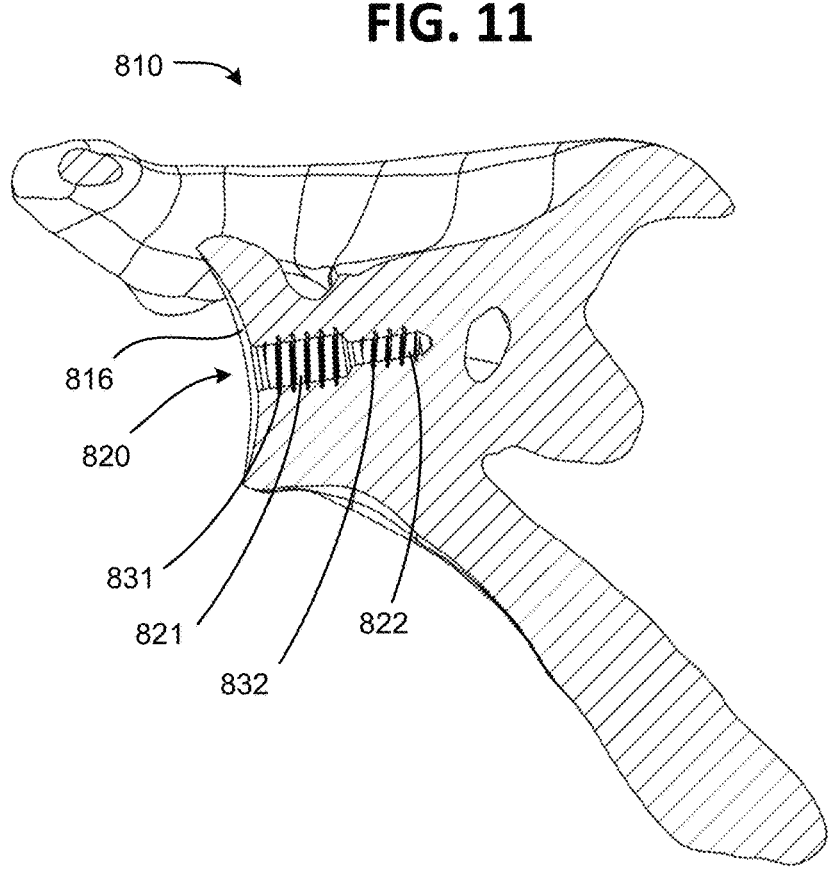
FIG. 12 illustrates a cross-sectional side view of the scapula bone of FIG. 11 taken along the line D-D shown in FIG. 11.

FIGS. 9-12 illustrate preparation of the scapula bone 810 during the example shoulder arthroplasty procedure. Specifically, FIG. 9 is a perspective view of the scapula bone 810 before preparation, FIG. 10 shows the scapula bone of FIG. 9 after glenoid preparation, FIG. 11 is a side view of the prepared scapula bone, and FIG. 12 shows a cross-sectional side view of the scapula bone of FIG. 11 taken along the line D-D in FIG. 11.

In some embodiments, the glenoid cavity 815 may be prepared by reaming a surface of the glenoid cavity 815 with a suitable reamer tool (not shown) to form a prepared glenoid surface 816.

In some embodiments, the prepared glenoid surface 816 may comprise a substantially flat surface.

In some embodiments, the prepared glenoid surface 816 may comprise a concave surface.

In some embodiments, the prepared glenoid surface 816 may comprise a concave semi-spherical surface.

In some embodiments, the glenoid cavity 815 may be further prepared by forming a glenoid bone tunnel 820 within the scapula bone 810 with one or more drill tools (not shown).

In some embodiments, the glenoid bone tunnel 820 may comprise a proximal bone tunnel portion 821 and a distal bone tunnel portion 822.

In some embodiments, a diameter of the proximal bone tunnel portion 821 may be sized and shaped to receive the first minor diameter 321 of the bone implant 300 therein (see FIG. 3D), and a diameter of the distal bone tunnel portion 822 may be sized and shaped to receive the second minor diameter 322 of the bone implant 300 therein.

In some embodiments, the diameter of the proximal bone tunnel portion 821 may be smaller than the first minor diameter 321 of the bone implant 300, and/or the diameter of the distal bone tunnel portion 822 may be smaller than the second minor diameter 322 of the bone implant 300.

In some embodiments, the diameter of the proximal bone tunnel portion 821 may be equal to the first minor diameter 321 of the bone implant 300, and/or the diameter of the distal bone tunnel portion 822 may be equal to the second minor diameter 322 of the bone implant 300.

In some embodiments, the diameter of the proximal bone tunnel portion 821 may be larger than the first minor diameter 321 of the bone implant 300, and/or the diameter of the distal bone tunnel portion 822 may be larger than the second minor diameter 322 of the bone implant 300.

In some embodiments, the proximal bone tunnel portion 821 may be tapped with a first bone tap tool (not shown) to form a first bone thread 831 about the proximal bone tunnel portion 821.

In some embodiments, the distal bone tunnel portion 822 may be tapped with a second bone tap tool (not shown) to form a second bone thread 832 about the distal bone tunnel portion 822.

It will be understood that the first bone thread 831 and/or the second bone thread 832 may be sized and shaped to receive any thread configuration, feature, or morphology described or contemplated herein with respect to any fastener/implant to achieve optimal fixation within a given bone/tissue.

Figures 13, 14:
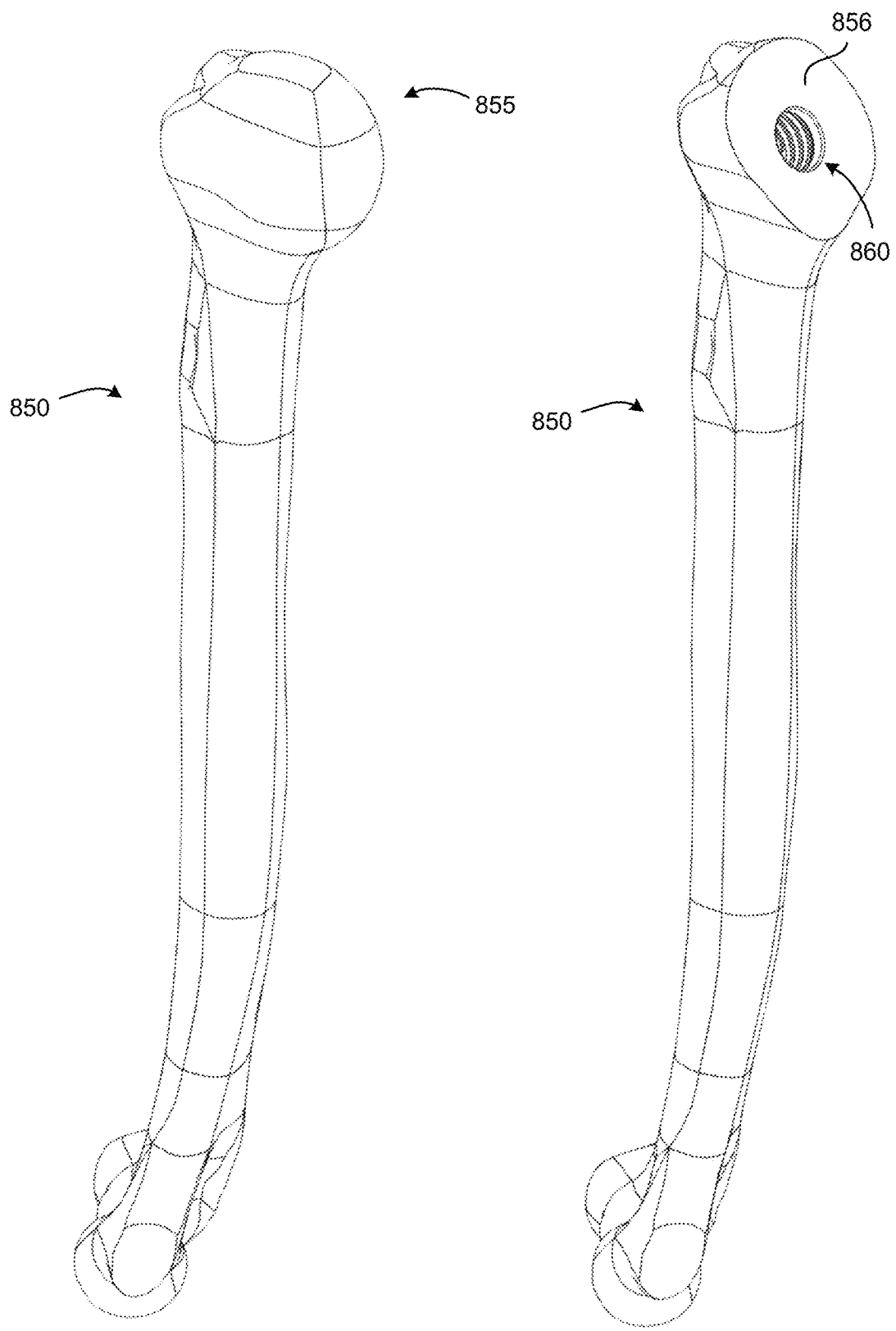
FIG. 13 illustrates a perspective view of a humeral bone of the shoulder joint of FIG. 8.
FIG. 14 illustrates the humeral bone of FIG. 13 with a prepared humeral head.

FIGS. 13-16 illustrate preparation of the humeral bone 850 during the example shoulder arthroplasty procedure. Specifically, FIG. 13 is a perspective view of the humeral bone 850 before preparation, FIG. 14 shows the humeral bone 850 with a prepared humeral head 855, FIG. 15 is a side view of the prepared humeral bone, and FIG. 16 is a cross-sectional side view of FIG. 15.

In some embodiments, the humeral head 855 may be prepared by cutting and/or reaming the humeral head 855 with a suitable cutter and/or reamer tool (not shown) to form a prepared humeral head surface 856.

In some embodiments, the prepared humeral head surface 856 may comprise a substantially flat surface.

In some embodiments, the prepared humeral head surface 856 may comprise a concave surface.

In some embodiments, the prepared humeral head surface 856 may comprise a concave semi-spherical surface.

In some embodiments, the humeral head 855 may be further prepared by forming a humeral bone tunnel 860 within the humeral head 855 with a drill tool (not shown).

In some embodiments, a diameter of the humeral bone tunnel 860 may be sized and shaped to receive the minor diameter 521 of the bone implant 500 (see FIG. 5E).

In some embodiments, the diameter of the humeral bone tunnel 860 may be smaller than the minor diameter 521 of the bone implant 500.

In some embodiments, the diameter of the humeral bone tunnel 860 may be equal to the minor diameter 521 of the bone implant 500.

In some embodiments, the diameter of the humeral bone tunnel 860 may be larger than the minor diameter 521 of the bone implant 500.

In some embodiments, the humeral bone tunnel 860 may be tapped with a bone tap tool (not shown) to form a bone thread 861 about the humeral bone tunnel 860.

It will be understood that the bone thread 861 may be sized and shaped to receive any thread configuration, feature, or morphology described or contemplated herein with respect to any fastener/implant to achieve optimal fixation within a given bone/tissue.

FIG. 17 shows the prepared shoulder joint bones before implant installation. FIG. 18 shows the prepared shoulder joint of FIG. 17 with the reverse shoulder arthroplasty system of FIG. 20 installed therein, and FIG. 19 shows a cross-sectional side view of FIG. 18. Alternatively, the anatomic shoulder arthroplasty system shown in FIG. 21 may be installed in the prepared shoulder joint of FIG. 17.

As noted above, FIGS. 20 and 21 illustrate front perspective views of the reverse shoulder arthroplasty system and the anatomic shoulder arthroplasty system, respectively. The reverse shoulder arthroplasty system shown in FIG. 20 may utilize the components shown and discussed in FIGS. 3A-3D and 5A-7B and installed in the shoulder joint 800 illustrated in FIG. 19. In this manner, the implant recess 590 of the bone implant 500 may receive the insert post 720 of the insert 700 therein, and the post recess 620 of the articulating head 600 may receive the implant post 390 of the bone implant 300 therein for the reverse shoulder arthroplasty system of FIG. 20.

Alternatively, the anatomic shoulder arthroplasty system shown in FIG. 21 may utilize components with complementary features to that of the reverse shoulder arthroplasty system shown in FIG. 20. For example, the post recess 620 of the articulating head 600 may receive the implant post 591 of the bone implant 500 therein, and the implant recess 391 of the bone implant 300 may receive the insert post 720 of the insert 700 therein for the anatomic shoulder arthroplasty system shown in FIG. 21.

Figure 22A:
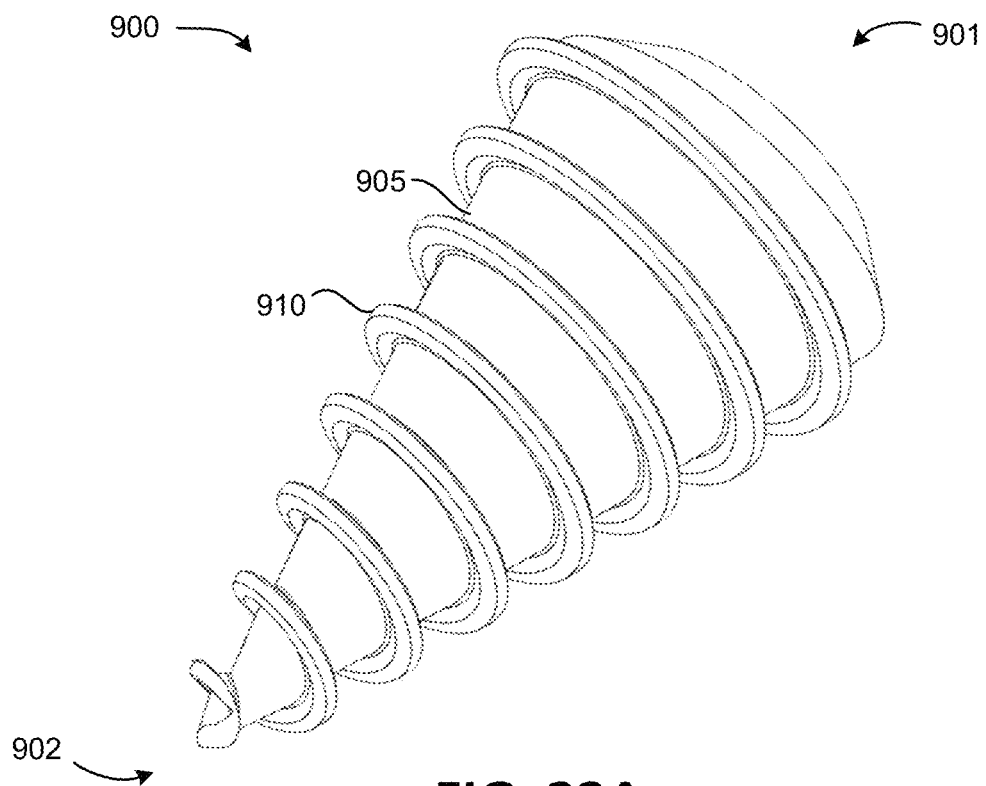
FIG. 22A illustrates a front perspective view of a bone implant, according to another embodiment of the present disclosure.
Figure 22B:
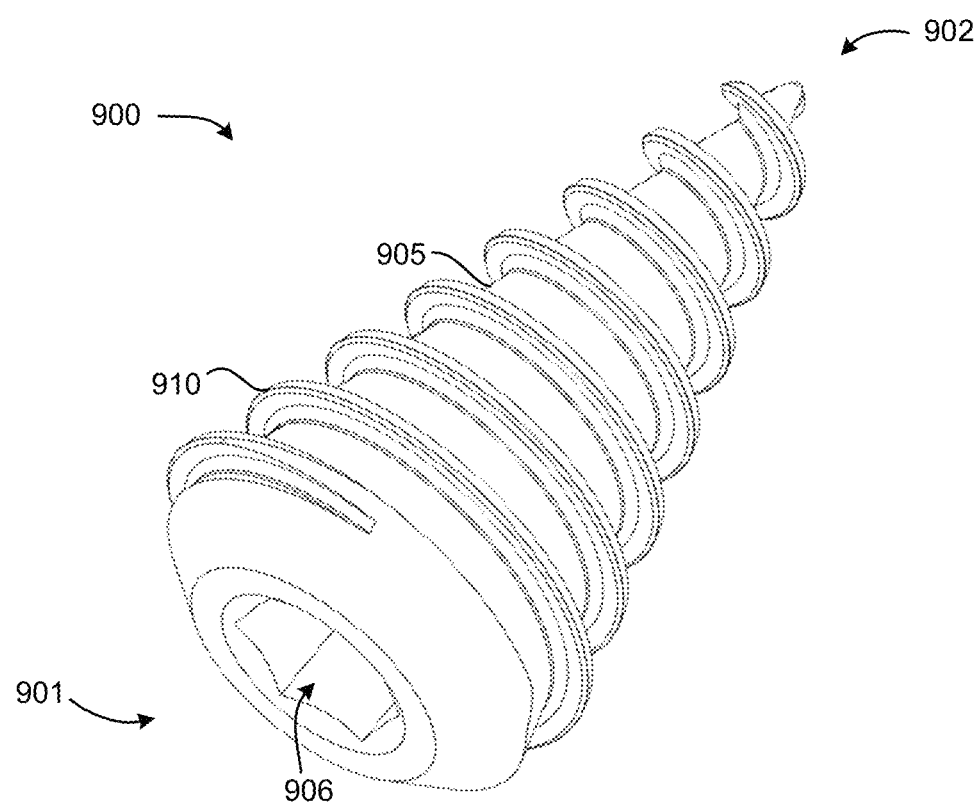
FIG. 22B illustrates a rear perspective view of the bone implant of FIG. 22A.
Figure 22C:
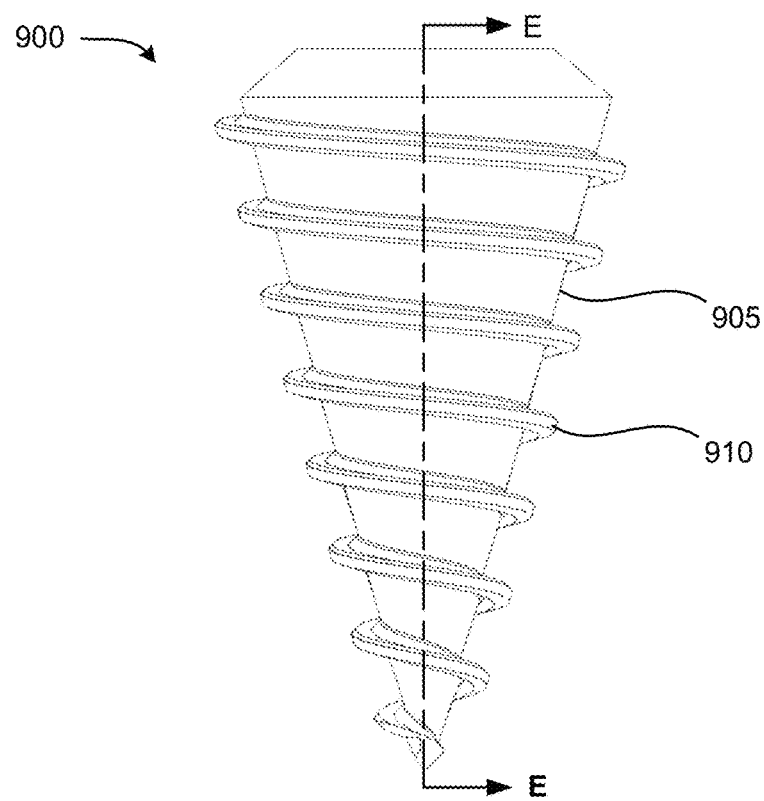
FIG. 22C illustrates a side view of the bone implant of FIG. 22A.
Figure 22D:
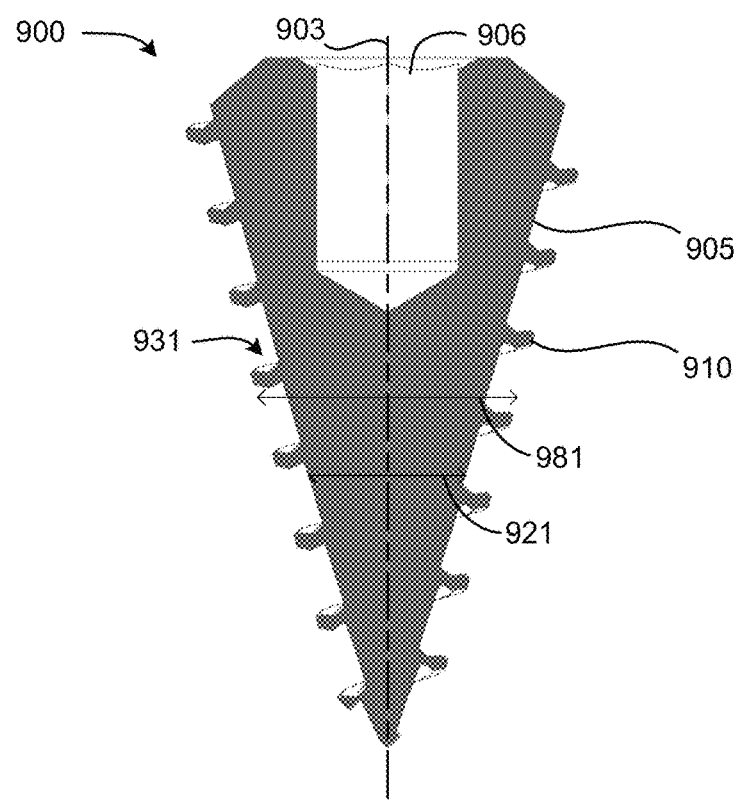
FIG. 22D illustrates a cross-sectional side view of the bone implant of FIG. 22A taken along the line E-E shown in FIG. 22C.

FIGS. 22A-22D illustrate various views of a fastener, implant, or bone implant 900, according to another embodiment of the present disclosure. Specifically, FIG. 22A is a front perspective view of the bone implant 900, FIG. 22B is a rear perspective view of the bone implant 900, FIG. 22C is a side view of the bone implant 900, and FIG. 22D is a cross-sectional side view of the bone implant 900 taken along the line E-E in FIG. 22C.

The bone implant 900 may generally include a tapered shaft 905 having a proximal end 901, a distal end 902, a longitudinal axis 903, at least one tapered helical thread 910 disposed about the tapered shaft, and a torque connection interface 906 formed in/on the proximal end 901 of the tapered shaft 905.

In some embodiments, the distal end 902 of the tapered shaft 905 may comprise a pointed or sharp tip.

In some embodiments, the tapered shaft 905 may comprise one or more self-tapping features or cutting flutes (not shown).

In some embodiments, the tapered shaft 905 may have a continuously variable minor diameter 921 generally defined by the shape of the tapered shaft 905, and a continuously variable major diameter 981 generally defined by the shape of the at least one tapered helical thread 910 disposed about the tapered shaft 905.

In some embodiments, the continuously variable minor diameter 921 defined by the shape of the tapered shaft 905 may comprise an at least partially conical shape.

In some embodiments, the continuously variable major diameter 981 defined by the shape of the at least one tapered helical thread 910 disposed about the tapered shaft 905 may comprise an at least partially conical shape.

In some embodiments, the continuously variable minor diameter 921 defined by the shape of the tapered shaft 905 may generally decrease moving from the proximal end 901 of the tapered shaft 905 toward the distal end 902 of the tapered shaft 905.

In some embodiments, the continuously variable major diameter 981 defined by the shape of the at least one tapered helical thread 910 disposed about the tapered shaft 905 may generally decrease moving from the proximal end 901 of the tapered shaft 905 toward the distal end 902 of the tapered shaft 905.

In some embodiments, the at least one tapered helical thread 910 may include at least one concave undercut surface 931.

In some embodiments, the at least one concave undercut surface 931 may be angled towards one of the proximal end 901 and the distal end 902 of the tapered shaft 905.

However, it will also be understood that the bone implant 900 may include any thread configuration, feature, or morphology described or contemplated herein with respect to any fastener/implant to achieve optimal fixation within a given bone/tissue. For example, in some embodiments the at least one tapered helical thread 910 may comprise standard or inverted threading, a "dual start" thread configuration, crescent shapes, etc.

Moreover, it will also be understood that the bone implant 900, or portions of the general design/shape of the bone implant 900, may be utilized in conjunction with (or within) any fastener, bone implant, system, or procedure that is described or contemplated herein. For example, any of the fasteners/bone implants described or contemplated herein may generally be configured to include a tapered shaft with tapered helical threading disposed about the tapered shaft. As one such non-limiting example, the design of the bone implant 300 shown in FIGS. 3A-3D may be modified to include a tapered shaft with tapered helical threading disposed about the tapered shaft in place of, or in addition to, the proximal shaft portion 308 and/or the distal shaft portion 309 previously discussed with reference to FIGS. 3A-3D, etc.

Any of the implants described or contemplated herein may be configured for removal and replacement during a revision procedure by simply unscrewing and removing the implant from the bone/tissue in which the implant resides. Moreover, the implants described herein may advantageously be removed from bone without removing any appreciable amount of bone during the removal process to preserve the bone. In this manner, implants may be mechanically integrated with the bone, while not being cemented to the bone or integrated via bony ingrowth, in order to provide an instant and removable connection between an implant and a bone. Accordingly, revision procedures utilizing the implants described herein can result in less trauma to the bone and improved patient outcomes. However, it will also be understood that any of the implants described or contemplated herein may also be utilized with cement, as desired.

Any procedures/methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A bone implant comprising:
   a shaft comprising:
      a proximal end;
      a distal end;
      a longitudinal axis;
      a proximal shaft portion comprising:
         a first minor diameter; and
         a first helical thread disposed about the proximal shaft portion defining a first major diameter of the proximal shaft portion, the first helical thread comprising a first concave undercut surface; and
      a distal shaft portion comprising:
         a second minor diameter; and
         a second helical thread disposed about the distal shaft portion defining a second major diameter of the distal shaft portion, the second helical thread comprising a second concave undercut surface,
      wherein:
         the first concave undercut surface and the second concave undercut surface are angled towards one of the proximal end and the distal end of the shaft;
         the first concave undercut surface extends from the first minor diameter of the proximal shaft portion to a first crest of the first helical thread disposed about the proximal shaft portion;
         the second concave undercut surface extends from the second minor diameter of the distal shaft portion to a second crest of the second helical thread disposed about the distal shaft portion;
         the first minor diameter of the proximal shaft portion is constant;
         the second minor diameter of the distal shaft portion is constant;
         the second minor diameter of the distal shaft portion is smaller than the first minor diameter of the proximal shaft portion; and
         the second major diameter of the distal shaft portion is smaller than the first major diameter of the proximal shaft portion.

2. The bone implant of claim 1, comprising a flange component at the proximal end of the shaft, the flange component comprising:
   a bone-facing surface; and
   an implement-facing surface.

3. The bone implant of claim 2, wherein the bone-facing surface comprises a convex surface.

4. The bone implant of claim 2, wherein the bone-facing surface comprises a semi-spherical surface.

5. The bone implant of claim 1, comprising an attachment feature at the proximal end of the shaft configured to secure an implement.

6. The bone implant of claim 5, wherein:
   the attachment feature comprises a post; and
   the implement comprises an articulating head comprising a convex semi-spherical articular surface, wherein the articulating head is configured to be removably couplable with the post.

7. The bone implant of claim 5, wherein:
   the attachment feature comprises an implant recess; and
   the implement comprises an insert having a concave semi-spherical articular surface, wherein the insert is configured to be removably couplable with the implant recess.

8. A bone implant comprising:
   a shaft comprising:
      a proximal end;
      a distal end;
      a longitudinal axis;
      a minor diameter; and
      a threaded shaft portion;
   an articulating member disposed at the proximal end of the shaft; and
   a helical thread disposed about the shaft defining a length of the threaded shaft portion, the helical thread comprising a concave undercut surface on a first side of the helical thread, and a convex undercut surface on a second side of the helical thread,
   wherein:
      the concave undercut surface extends from the minor diameter of the shaft to a crest of the helical thread on the first side of the helical thread;
      the convex undercut surface extends from the minor diameter of the shaft to the crest of the helical thread on the second side of the helical thread;
      the concave undercut surface is angled towards one of the proximal end and the distal end of the shaft; and
      a ratio of the length of the threaded shaft portion to the minor diameter of the shaft is less than 1.50.

9. The bone implant of claim 8, wherein the ratio of the length of the threaded shaft portion to the minor diameter of the shaft is less than 1.25.

10. The bone implant of claim 8, wherein the ratio of the length of the threaded shaft portion to the minor diameter of the shaft is less than 1.10.

11. The bone implant of claim 8, wherein the ratio of the length of the threaded shaft portion to the minor diameter of the shaft is equal to 1.0.

12. The bone implant of claim 8, wherein the ratio of the length of the threaded shaft portion to the minor diameter of the shaft is less than 1.0.

13. The bone implant of claim 8, further comprising:
a flange component at the proximal end of the shaft, the flange component comprising:
a bone-facing surface; and
an implement-facing surface.

14. The bone implant of claim 8, wherein the articulating member is configured to be removably couplable with an attachment feature at the proximal end of the shaft.

15. A shoulder joint implant comprising:
a shaft comprising:
a proximal end;
a distal end; and
a longitudinal axis;
a helical thread disposed about the shaft along the longitudinal axis between the proximal and distal ends of the shaft, the helical thread comprising:
a first undercut surface;
a second undercut surface;
a third undercut surface; and
a fourth open surface, wherein:
the helical thread does not have mirror symmetry with itself across any plane perpendicular to the longitudinal axis of the shaft;
at least one of the first undercut surface, the second undercut surface, the third undercut surface, and the fourth open surface comprises a flat surface;
the first undercut surface and the third undercut surface are angled towards one of the proximal end and the distal end of the shaft; and
the second undercut surface and the fourth open surface are angled towards the other one of the proximal end and the distal end of the shaft; and
a shoulder joint implement comprising an articular surface at the proximal end of the shaft.

16. The shoulder joint implant of claim 15, wherein:
the shoulder joint implement comprises a glenoid head prosthesis; and
the articular surface comprises a convex semi-spherical articular surface.

17. The shoulder joint implant of claim 15, wherein:
the shoulder joint implement comprises a humeral head prosthesis; and
the articular surface comprises a convex semi-spherical articular surface.

18. The shoulder joint implant of claim 15, wherein:
the shoulder joint implement comprises a glenoid insert prosthesis; and
and the articular surface comprises a concave semi-spherical articular surface.

19. The shoulder joint implant of claim 15, wherein:
the shoulder joint implement comprises a humeral insert prosthesis; and
the articular surface comprises a concave semi-spherical articular surface.

20. The shoulder joint implant of claim 15, comprising a flange component at the proximal end of the shaft, the flange component comprising:
a bone-facing surface; and
an implement-facing surface.

21. The bone implant of claim 1, wherein the second major diameter of the distal shaft portion is smaller than the first minor diameter of the proximal shaft portion.

22. The bone implant of claim 8, wherein the minor diameter of the shaft is constant.

23. The shoulder joint implant of claim 15, wherein:
the first undercut surface and the second undercut surface form a concave undercut surface on a first side of the helical thread; and
the third undercut surface and the fourth open surface form a convex undercut surface on a second side of the helical thread.

24. A bone implant comprising:
a shaft comprising:
a proximal end;
a distal end;
a longitudinal axis;
a proximal shaft portion comprising:
a first minor diameter; and
a first helical thread disposed about the proximal shaft portion defining a first major diameter of the proximal shaft portion, the first helical thread comprising a first concave undercut surface; and
a distal shaft portion comprising:
a second minor diameter; and
a second helical thread disposed about the distal shaft portion defining a second major diameter of the distal shaft portion, the second helical thread comprising a second concave undercut surface,
wherein:
the first helical thread does not have mirror symmetry with itself across any plane perpendicular to the longitudinal axis of the shaft;
the second helical thread does not have mirror symmetry with itself across any plane perpendicular to the longitudinal axis of the shaft;
the first concave undercut surface and the second concave undercut surface are angled towards one of the proximal end and the distal end of the shaft;
the second minor diameter of the distal shaft portion is smaller than the first minor diameter of the proximal shaft portion forming a shoulder intermediate the proximal shaft portion and the distal shaft portion; and
the second major diameter of the distal shaft portion is smaller than the first major diameter of the proximal shaft portion.

25. The bone implant of claim 24, wherein the second major diameter of the distal shaft portion is smaller than the first minor diameter of the proximal shaft portion.

26. The bone implant of claim 24, wherein:
the first minor diameter of the proximal shaft portion is constant; and
the second minor diameter of the distal shaft portion is constant.

27. A bone implant comprising:
a shaft comprising:
a proximal end;
a distal end;
a longitudinal axis;
a minor diameter; and
a threaded shaft portion;
an articulating member disposed at the proximal end of the shaft; and a helical thread disposed about the shaft defining a length of the threaded shaft portion, the helical thread comprising a concave undercut surface, wherein:

the concave undercut surface is angled towards one of the proximal end and the distal end of the shaft; and the concave undercut surface is formed by a first undercut surface, a second undercut surface, and an inflection point intermediate the first undercut surface and the second undercut surface, wherein the first undercut surface extends from the minor diameter of the shaft to the inflection point, and the second undercut surface extends from the inflection point to a crest of the helical thread.

28. The bone implant of claim 27, wherein the minor diameter of the shaft is constant.

29. The bone implant of claim 27, wherein:

the concave undercut surface is positioned on a first side of the helical thread; and the helical thread comprises a convex undercut surface positioned on a second side of the helical thread.

30. A shoulder joint implant comprising:

a shaft comprising:
 a proximal end;
 a distal end; and
 a longitudinal axis;

a helical thread disposed about the shaft along the longitudinal axis between the proximal and distal ends of the shaft, the helical thread comprising:
 a first undercut surface;
 a second undercut surface adjacent the first undercut surface forming a first inflection point intermediate the first undercut surface and the second undercut surface;
 a third undercut surface; and
 a fourth open surface adjacent the third undercut surface forming a second inflection point intermediate the third undercut surface and the fourth open surface, wherein:

the first undercut surface extends from a minor diameter of the shaft to the first inflection point, and the second undercut surface extends from the first inflection point to a crest of the helical thread;

the third undercut surface extends from the minor diameter of the shaft to the second inflection point, and the fourth open surface extends from the second inflection point to the crest of the helical thread;

the first undercut surface and the third undercut surface are angled towards one of the proximal end and the distal end of the shaft; and the second undercut surface and the fourth open surface are angled towards the other one of the proximal end and the distal end of the shaft; and a shoulder joint implement comprising an articular surface at the proximal end of the shaft.

31. The shoulder joint implant of claim 30, wherein:

the first undercut surface and the second undercut surface form a concave undercut surface on a first side of the helical thread; and the third undercut surface and the fourth open surface form a convex undercut surface on a second side of the helical thread.

32. The shoulder joint implant of claim 30, wherein at least one of the first undercut surface, the second undercut surface, the third undercut surface, and the fourth open surface comprises a flat surface.

* * * * *